(12) United States Patent
Ueda

(10) Patent No.: US 9,023,835 B2
(45) Date of Patent: May 5, 2015

(54) AGENT FOR AMELIORATING BLOOD-BRAIN BARRIER DISORDERS

(75) Inventor: Hiroshi Ueda, Nagasaki (JP)

(73) Assignee: Nagasaki University, Nagasaki (JP)

( * ) Notice: Subject to any disclaimer, the term of this patent is extended or adjusted under 35 U.S.C. 154(b) by 199 days.

(21) Appl. No.: 13/390,058

(22) PCT Filed: Aug. 9, 2010

(86) PCT No.: PCT/JP2010/063501
§ 371 (c)(1),
(2), (4) Date: Mar. 7, 2012

(87) PCT Pub. No.: WO2011/019023
PCT Pub. Date: Feb. 17, 2011

(65) Prior Publication Data
US 2012/0165259 A1   Jun. 28, 2012

(30) Foreign Application Priority Data

Aug. 10, 2009 (JP) .................... 2009-185816

(51) Int. Cl.
A61K 38/22 (2006.01)
A61K 45/06 (2006.01)

(52) U.S. Cl.
CPC ............. *A61K 38/2292* (2013.01); *A61K 45/06* (2013.01)

(58) Field of Classification Search
CPC ................ A61K 2300/00; A61K 38/2292
See application file for complete search history.

(56) References Cited

FOREIGN PATENT DOCUMENTS

WO    WO 2004/064861 A1    8/2004

OTHER PUBLICATIONS

Fujita et al. "Prothymosin-a1 prevents necrosis and apoptosis following stroke", Cell Death and Differentiation, 2007, pp. 1839-1842).*
Wang et al. "Role of MC-1 alone and in combination with tissue plasminogen activator in focal ischemic brain injury in rats", J Neurosurg, 2005, pp. 165-169.*
Ueda, WO 2004/064861 A1; published 2004; machine translation provided; obtained Mar. 1, 2014 from the JPO/INT, document page No. 1-26.*
Ueda "Prothymosin a plays a key role in cell death mode-switch, a new concept for neuroprotective mechanisms in stroke", Naunyn-Schmiedeberg's Arch Pharmacol, 2008, pp. 315-323.*
GenBank Accession No. AAB08707.1, obtained from http://www.ncbi.nlm.nih.gov/protein/AAB08707.1 on Sep. 13, 2014, p. 1.*
Levin et al., The expressing of endothelial tissue plasminogen activator in vivo: a function defined by vessel size and anatomic location, J Cell Sci, 1997, pp. 139-148.*
Japanese Patent Office, Written Opinion in International Patent Application No. PCT/JP2010/063501 (Oct. 19, 2010).
Fujita et al., *Cell Death and Differentiation*, 14: 1839-1842 (2007).
Fujita et al., *Cell Death and Differentiation*, 16: 349-358 (2009).
Ueda, Hiroshi, *Medical Bio*, 83-89 (Mar. 2008).
Ueda et al., *Folia Pharmacological Japonica*, 119: 79-88 (2002).
Ueda et al., *Journal of Cell Biology*, 176(6): 853-862 (2007).
Ueda, Hiroshi, *Pharmacology & Therapeutics*, 123(3): 323-333 (2009).
Yomiuri Shimbun Online, Modern Medical Care: Medical Care: Medical Care and Nursing: "New Medicine tPA for Cerebral Infarction," http://www.yomiuri.co.jp/iryou/medi/saisin/20051025ik14.htm (Oct. 25, 2005).
Japanese Patent Office, International Search Report in International Patent Application No. PCT/JP2010/063501 (Oct. 19, 2010).

* cited by examiner

*Primary Examiner* — Karlheinz R Skowronek
*Assistant Examiner* — Lianko Garyu
(74) *Attorney, Agent, or Firm* — Leydig, Voit & Mayer, Ltd.

(57) ABSTRACT

The invention provides a method of ameliorating a blood-brain barrier disorder, as well as a method of treating a disease accompanied by a blood-brain barrier disorder and a method of treating a cerebral ischemic disease, by administering a prothymosin α, or a protein or polypeptide possessing the same function as the prothymosin α. The invention also provides polypeptides useful in the context of the aforesaid methods.

15 Claims, 17 Drawing Sheets

FIG. 1-1

| | |
|---|---|
| rat active form (SEQ ID NO: 4) | MSDAAVDTSSEITTEDLKEKKEVVEEAENGRDAPAHGNA |
| human 1 (liver) | MSDAAVDTSSEITTKDLKEKKEVVEEAENGRDAPANGNA |
| human 2 (thymus) | MSDAAVDTSSEITTKDLKEKKEVVEEAENGRDAPANGNA |
| human 3 (thymus) | MSDAAVDTSSEITTKDLKEKKEVVEEAENGRDAPANGNA |
| human 4 (pancreas, adenocarcinoma) | MSDAAVDTSSEITTEDLKEKKEVVEEAENGRDAPANRNA |
| human 5 (lymphocyte) | MSDAAVDTSSEITIKDLKEKKEVVEEAENGRDAPANGNA |
| human 6 (lymphocyte) | MSDAAVDTSSEITTKDLQEKKEVVEEAENGRDAPANGNA |
| human 7 (lymphocyte) | MSDAAVDTSSEITTKDLKEKKEVVEEAENGRDAPA |
| human 8 (lymphocyte) | MSDAAVDTSSEITTKDLQEKKEVVEEAENGRDAPANGNA |
| human 9 (lymphocyte) | MSDAAVDTSSEITTKDLKEKKEVVEEAENGRDAPANGNAE |
| human 10 (lymphocyte) | MSDAAVDTSSEITTKDLKEKKEVVEEAENGRDAPANGNA |
| human 11 (lymphocyte) | MSDAAVDTSSEITTKDLKEKKEVVEEAENGRDAPANGNAE |
| human 12 (lymphocyte) | MSDAAVDTSSEITTKDLKEKKEVVEEAENGRDAPANGNA |
| human 13 (lymphocyte) | MSDAAVDTSSEITTKDLKEKKEVVEEAENGRDAPANGNA |
| human 14 (lymphocyte) | MSDAAVDTSSEITTKDLKEKKEVVEEAENGRDAPANGNA |
| human 15 (lymphocyte cell line) | MSDAAVDTSSEITTKDLKEKKEVVEEAENGRDAPANGNA |
| human 16 (peripheral T cells) | MSDAAVDTSSEITTKDLKEKKEVVEEAENGRDAPANGNA |
| human 17 (tonsil -derived primary B cells) | MSDAAVDTSSEITTKDLKEKKEVVEEAENGRDAPANGNA |
| human 18 (spleen) | MSDAAVDTSSEITTKDLKEKKEVVEEAENGRDAPANGNA |
| human 19 (fibroblast cell line) | MSDAAVDTSSEITTKDLKEKKEVVEEAENGRDAPANGNAE |
| human 20 (primitive neuroectodermal tumor) | MSDAAVDTSSEITTKDLKEKKEVVEEAENGRDAPANGNA |
| human 21 (primitive neuroectodermal tumor) | MSDAAVDTSSEITTKDLKEKKEVVEEAENGRDAPANGNA |
| human 22 | MSDAAVDTSSEITTEDLKEKKEVVEEAENGRDAPA |
| human 23 | MSDAAVDTSSEITTEDLKEKKEVVEEAENGRDAPA |
| | |
| rat1 (spleen) | MSDAAVDTSSEITTKDLKEKKEVVEEAENGRDAPANGNAQ |
| rat2 (spleen) | MSDAAVDTSSEITTKDLKEKKEVVEEAENGRDAPANGNAQ |
| rat3 (fibroblast) | MSDAAVDTSSEITTKDLKEKKEVVEEAENGRDAPANGNAQ |
| rat4 (fibroblast) | MSDAAVDTSSEITTKDLKEKKEVVEEAENGRDAPANGNAQ |
| rat5 | MSDAAVDTSSEITTKDLKEKKEVVEEAENGRDAPANGNAQ |
| rat6 (ovary) | MSDAAVDTSSEITTKDLKEKKEVVEEAENGRDAPANGNAQ |
| rat7 (ovary) | MSDAAVDTSSEITTKDLKEKKEVVEEAENGRDAPANGNAQ |
| | |
| mouse1 (16days neonatethymus) | MSDAAVDTSSEITTKDLKEKKEVVEEAENGRDAPANGNAQ |
| mouse2 (16days neonatethymus) | MSDEAVDTSSEITTKDLNEKEEVVEEAESGRDAPANGNAQ |
| mouse3 (Ehrlich ascites tumor cell) | MSDAAVDTSSEITTKDLKEKKEVVEEAENGRDAPANGNAQ |
| mouse4 (Ehrlich ascites tumor cell) | MSDAAVDTSSEITTKDLKEKKEVVEEAENGRDAPANGNAQ |
| | MSDAAVDTSSEITTKDLKEKKEVVEEAENGRDAPANGNAQ |
| | |
| zebrafish (embryonic hematopoietic progenitor cell) | MADTKVDTNKDVSAKDLKEKKQV EEAENGKDAPANGNAE |
| edible frog (testis) | MSDTSVDASVEKTTKDLKSKDKELVEETENGKDKPANGNA |

FIG. 1-2

| | |
|---|---|
| rat active form (SEQ ID NO: 4) | ADNEVDEEEEEGGEEEEEEEEGDGEEEDGD |
| human 1 (liver) | NEENGEPEADNEVDEEEEEGGEEE    GDGEEEDGD |
| human 2 (thymus) | NEENGEQEADNEVDEEEEEGGEEEEEEEEGDGEEEDGD |
| human 3 (thymus) | NEENGEQEADNEVDEEEEEGGEEEEEEEEGDGEEVDGD |
| human 4 (pancreas, adenocarcinoma) | NEENGEQEADNEVDEEEEEGGEEEEEEEGDGEEEDGD |
| human 5 (lymphocyte) | NEENGEPEADNEVDEEEEEGGEEEEEE  GDGEEEDGD |
| human 6 (lymphocyte) | NEENGEQEADSEVDEEEEEGGEEEEEEEEGDGEEEDGD |
| human 7 (lymphocyte) | NEENGEQEADNEVDEEEEEGGEEEEEE  GDGEEEDGD |
| human 8 (lymphocyte) | DEENGEQEADNEVDEEQEEGGEEEEEEEEGEGEEE |
| human 9 (lymphocyte) | NEENGEQEADSEVDEEEEEGGEEEEEEEEGDGEEEDGD |
| human 10 (lymphocyte) | NEENGEQEADNEVDEEEEEGGEEEEEEEEGDGEEEDGD |
| human 11 (lymphocyte) | NEENGEQEADNEVDEEEEEGGEEEEEEEEGDGEEEDGD |
| human 12 (lymphocyte) | NEENGEQEADNEVDEEEEEGGEEEEEEEEGDGEEEDGD |
| human 13 (lymphocyte) | NEENGEQEADNEVDEEEEEGGEEEEEEEEGDGEEEDGD |
| human 14 (lymphocyte) | NEENGEQEADNEVDEEEEEGGEEEEEEEEGDGEEEDGD |
| human 15 (lymphocyte cell line) | NEENGEQEADNEVDEEEEEGGEEEEEEEEGDGEEEDGD |
| human 16 (peripheral T cells) | NEENGEQEADNEVDEEEEEGGEEEEEEEEGDGEEEDGD |
| human 17 (tonsil -derived primary B cells) | NEENGEQEADNEVDEEEEEGGEEEEEEEEGDGEEEDGD |
| human 18 (spleen) | NEENGEQEADNEVDEEEEEGGEEEEEEEEGDGEEEDGD |
| human 19 (fibroblast cell line) | NEENGEQEADNEVDEEEEEGGEEEEEEEEGDGEEEDGD |
| human 20 (primitive neuroectodermal tumor) | NEENGEQEADNEVDEEEEEGGEEEEEEEEGDGEEEGGD |
| human 21 (primitive neuroectodermal tumor) | NEENGEQEADNEVDEEEEEGGEEEEEEEEGDGEEEGGD |
| human 22 | DEENGEQEADNEVDEEQEEGGEEE    GDGEEEDGD |
| human 23 | DEENGEQEADNEVDEEQEEGGEEE    GDGEEEDGD |
| rat1 (spleen) | NEENGEQEADNEVDEEEEEGGEEEEEEEEGDGEEEDGD |
| rat2 (spleen) | NEENGEQEADNEVDEEEEEGGEEEEEEEEGDGEEEDGD |
| rat3 (fibroblast) | NEENGEQEADNEVDEEEEEGGEEEEEEEEGDGEEEDGD |
| rat4 (fibroblast) | NEENGEQEADNEVDEEEEEGGEEEEEEEEGDGEEEDGD |
| rat5 | NEENGEQEADNEVDEEEEEGGEEEEEEEEGDGEEEDGD |
| rat6 (ovary) | NEENGEQEADNEVDEEEEEGGEEEEEEEEGDGEEEDGD |
| rat7 (ovary) | NEENGEQEADNEVDEEEEEGGEEKEEEKEGDGEEEDGD |
| mouse1 (16days neonatethymus) | NEENGEQEADNEVDEEEEEGGEEEEEEEEGDGEEEDGD |
| mouse2 (16days neonatethymus) | NEENGEQEAGNEVDEEEEE    GDGEEEDGD |
| mouse3 (Ehrlich ascites tumor cell) | NEENGEQEADNEVDEEEEEGGEEEEEEEEGDGEEEDGD |
| mouse4 (Ehrlich ascites tumor cell) | NEENGEQEADNEVDEEEEEGGEEEEEEEEGDGEEEDGD |
| | NEENGEQEADNEVDEEEEEGGEEEEEEEEGDGEEEDGD |
| zebrafish (embryonic hematopoietic progenitor cell) | NEENGDQE  NEVDEEDDDVAEEDEED    DGEGDDDD |
| edible frog (testis) | ENEENGEDGADNEEEEE VDEEDEEDEGEGDDDE    GD |

FIG. 1-3

| | |
|---|---|
| rat active form (SEQ ID NO: 4) | |
| human 1 (liver) | EDEGAESATGKRAAEDDEDDDVDTQKQK TDEDD |
| human 2 (thymus) | EDEEAESATGKRAAEDDEDDDVDTKKQK TDEDD |
| human 3 (thymus) | EDEEAESATGKRAAEDDEDDDVDTKKQK TDEDD |
| human 4 (pancreas, adenocarcinoma) | EDEEAESATGKRAAEDDEDDDVDTKKQK TDEDD |
| human 5 (lymphocyte) | EDEGAESATGKRAAEDDEDDDVDTQKSE DRRG |
| human 6 (lymphocyte) | EDEEAESPTGKRAAEDDEDDDVDTKKQK TDEDD |
| human 7 (lymphocyte) | EDEEAETATGKRAAEDDEDDDVDTKKQK TDEDD |
| human 8 (lymphocyte) | GWR |
| human 9 (lymphocyte) | EDEEAESATGKRAAEDDEDDDVDTKKQK TDEDD |
| human 10 (lymphocyte) | EDEEAESATGKRAAEDDEDDDVDTKKQK TDEDD |
| human 11 (lymphocyte) | EDEEAESATGKRAAEDDEDDDVDTKKQK TDEDD |
| human 12 (lymphocyte) | EDEEAESATGKRAAEDDEDDDVDTKKQK TDEDD |
| human 13 (lymphocyte) | EDEEAESATGKRAAEDDEDDDVDTKKQK TDEDD |
| human 14 (lymphocyte) | EDEEAESATGK |
| human 15 (lymphocyte cell line) | EDEEAESATGKRAAEDDEDDDVDTKKQK TDEDD |
| human 16 (peripheral T cells) | EDEEAESATGKRAAEDDEDDDVDTKKQK TDEDD |
| human 17 (tonsil -derived primary B cells) | EDEEAESATGKRAAEDDEDDDVDTKKQK TDEDD |
| human 18 (spleen) | EDEEAESATGKRAAEDDEDDDVDTKKQK TDEDD |
| human 19 (fibroblast cell line) | EDEEAESATGKRAAEDDEDDDVDTKKQK TDEDD |
| human 20 (primitive neuroectodermal tumor) | EDEEAESATGKRAAEDDEDDDVDTKKQK TDEDD |
| human 21 (primitive neuroectodermal tumor) | EDEEAESATGKRAAEDDEDDDVDTKKQK TDEDD |
| human 22 | EDEGAESATDKRAAEDDEDNDVDTKKQK TDEDD |
| human 23 | EDEGAESATDKRAAEDDEDNDVDTKKQK TDEDD |
| | |
| rat1 (spleen) | EDEEAEAPTGKRVAEDDEDDDVETKKQKKTDEDD |
| rat2 (spleen) | EDEEAEAPTGKRVAEDDEDDDVETKKQKKTDEDD |
| rat3 (fibroblast) | EDEEAEAPTGKRVAEDDEDDDVETKKQKKTDEDD |
| rat4 (fibroblast) | EDEEAEAPTGKRVAEDDEDDDVETKKQKKTDEDD |
| rat5 | EDEEAEAPTGKRVAEDDEDDDVETKKQKKTDEDD |
| rat6 (ovary) | EDEEAGQKK |
| rat7 (ovary) | EDEEAGQKK |
| | |
| mouse1 (16days neonatethymus) | EDEEAEAPTGKRVAEDDEDDDVDTKKQK TEEDD |
| mouse2 (16days neonatethymus) | EDEEAEAPTGKRVAEDDEDDDVDTKKQK TEEDD |
| mouse3 (Ehrlich ascites tumor cell) | EDEEAEAPTGKRVAEDDEDDDVDTKKQK TEEDD |
| mouse4 (Ehrlich ascites tumor cell) | EDEEAEAPTGKRVAEDDEDDDVDTKKQK TEEDD |
| | EDEEAEAPTGKRVAEDDEDDDVDTKKQK TEEDD |
| | |
| zebrafish (embryonic hematopoietic progenitor cell) | EDEEAEGGTGKRAAEDDDDDEDDVDPKKQKTDV |
| edible frog (testis) | EDDEADGATGKRAAEDDDEDDDVDAKKQKTDDDD |

FIG. 2

|  | 10 | 20 | 30 | 40 | 50 | 60 |
|---|---|---|---|---|---|---|
| human-derived prothymosin α | MSDAAVDTSS | EITTEDLKEK | KEVVEEAENG | RDAPAHGNA- | NEENGEPEAD | NEVDEEEEEG |
| rat-derived prothymosin α | MSDAAVDTSS | EITTKDLKEK | KEVVEEAENG | RDAPANGNAQ | NEENGEQEAD | NEVDEEEEEG |
| mouse-derived prothymosin α | MSDAAVDTSS | EITTKDLKEK | KEVVEEAENG | RDAPANGNAQ | NEENGEQEAD | NEVDEEEEEG |
| thymosin | SDAAVDTSS | EITTKDLKEK | KEVVEEAEN | | | |

|  | 70 | 80 | 90 | 100 | 110 |  |
|---|---|---|---|---|---|---|
| human-derived prothymosin α | GEEE-----G | DGEEEDGDED | EGAESATGKR | AAEDDEDDDV | DTQKQK-TDE | DD |
| rat-derived prothymosin α | GEEEEEEEEG | DGEEEDGDED | EEAEAPTGKR | VAEDDEDDDV | ETKKQKKTDE | DD |
| mouse-derived prothymosin α | GEEEEEEEG | DGEEEDGDED | EEAEAPTGKR | VAEDDEDDDV | DTKKQK-TEE | DD |

FIG. 3
A
contra | ipsi
30min
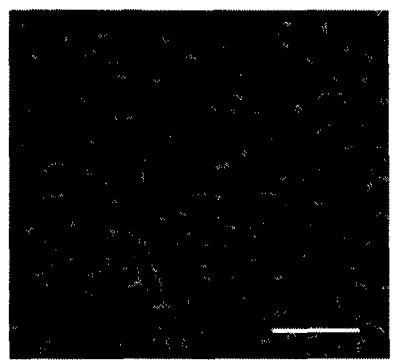 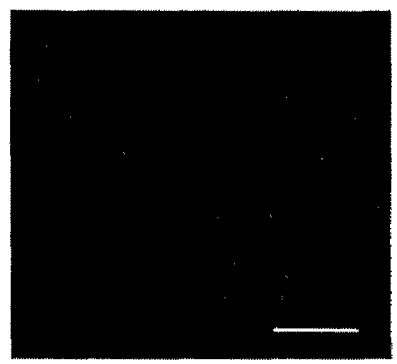
60min
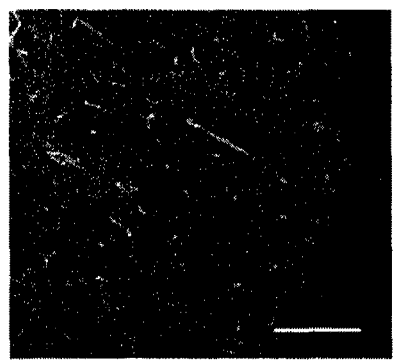 
B
Veh | ProTα
cortex
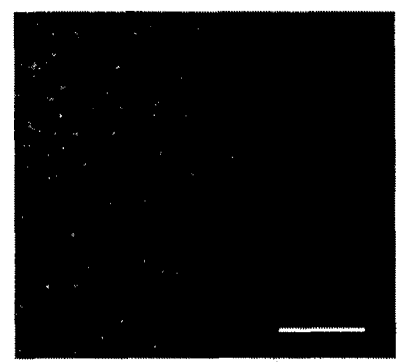 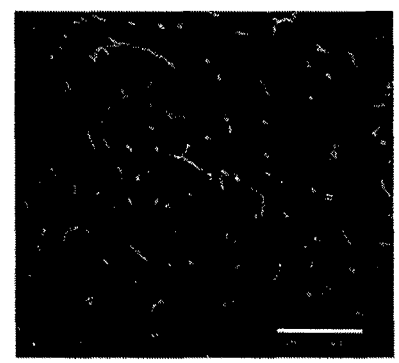
striatum
 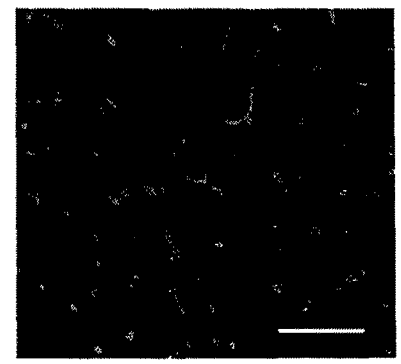

FIG. 7
A
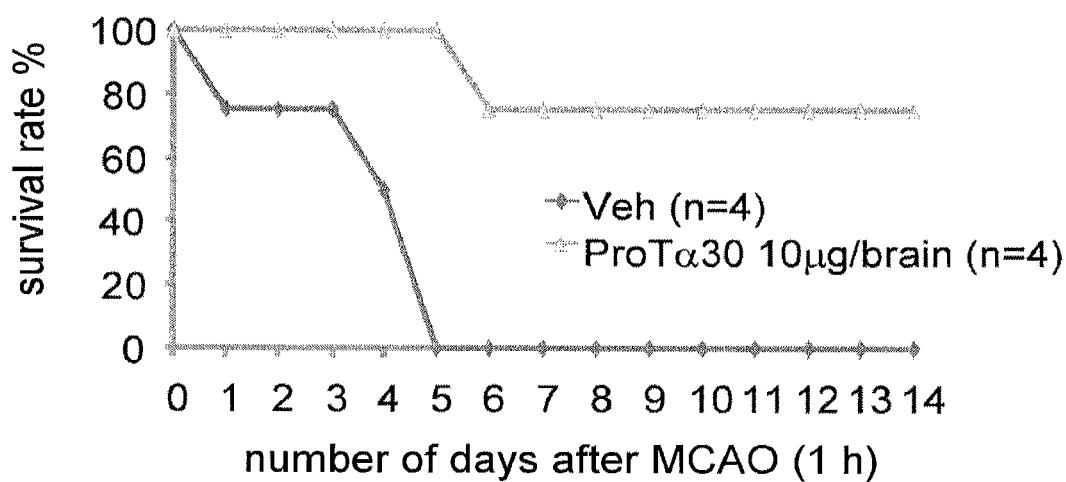
B
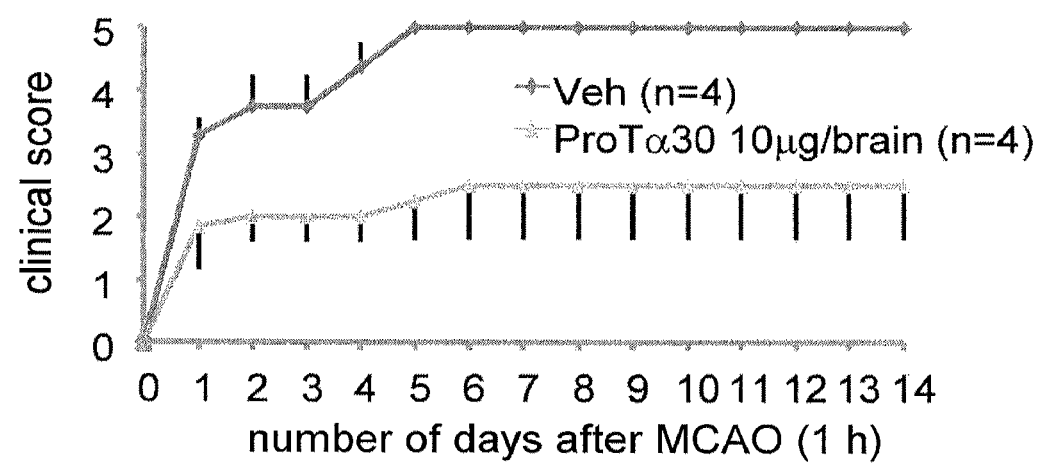

FIG. 8
A
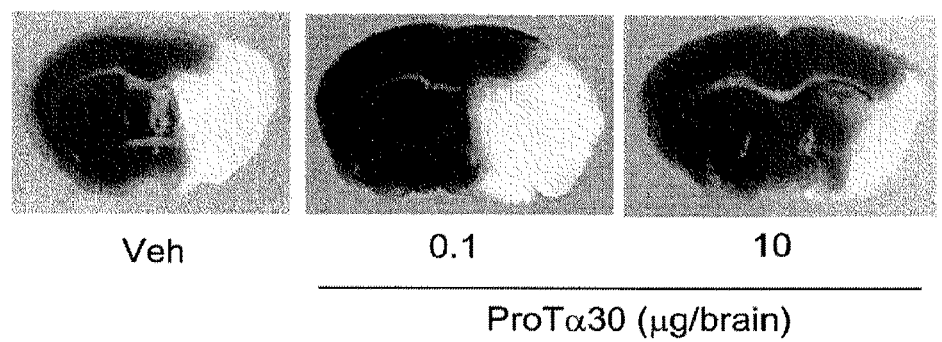
B
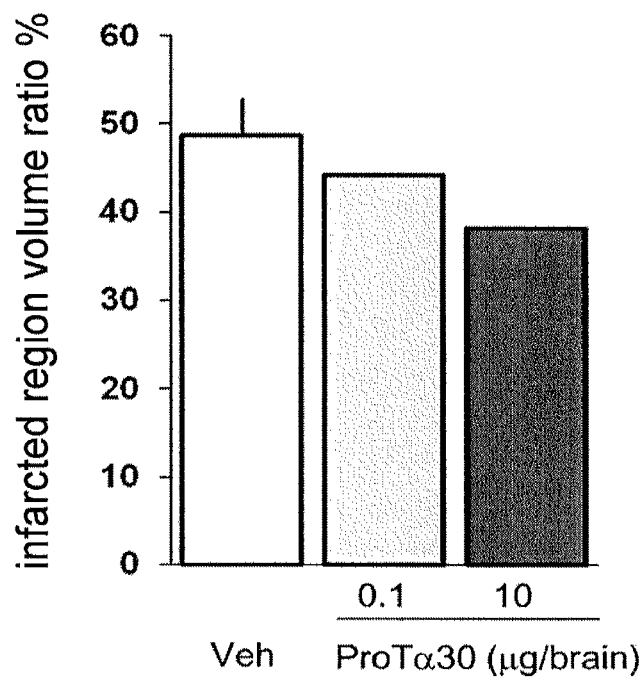

FIG. 9
A
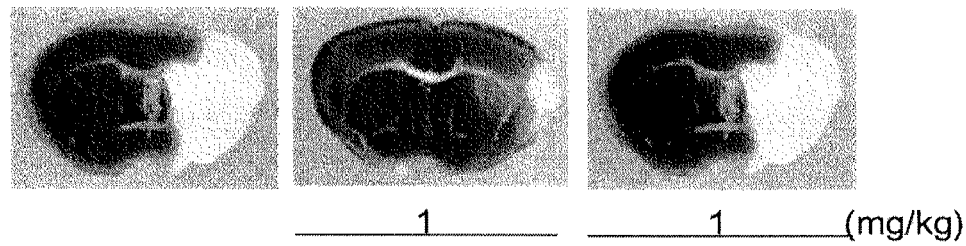
B
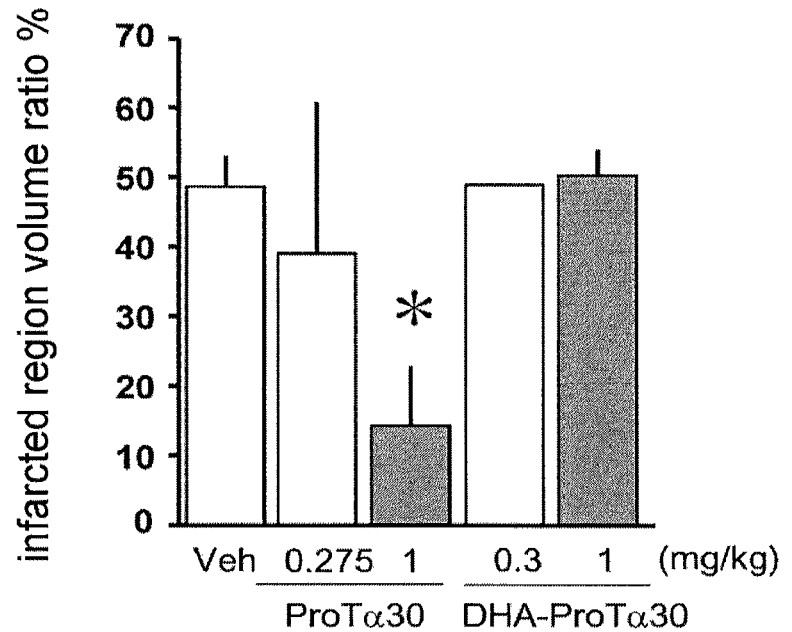
C
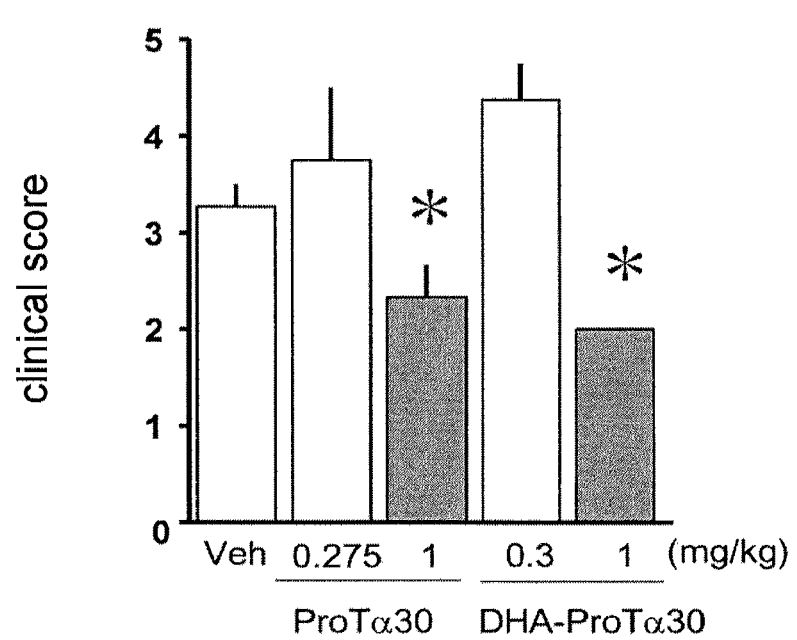

FIG. 10
A 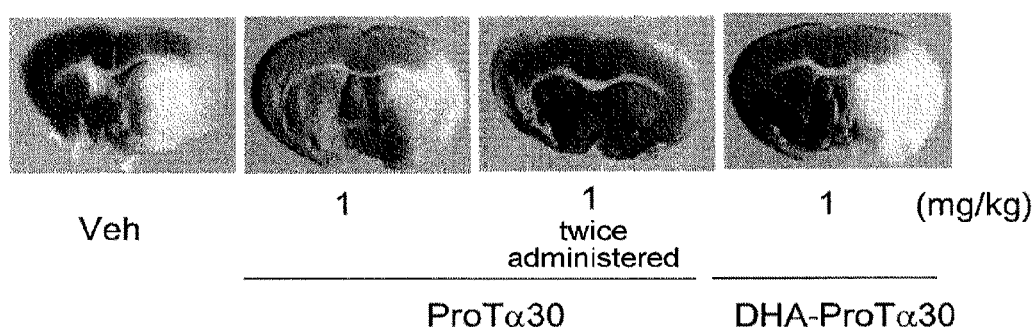
B 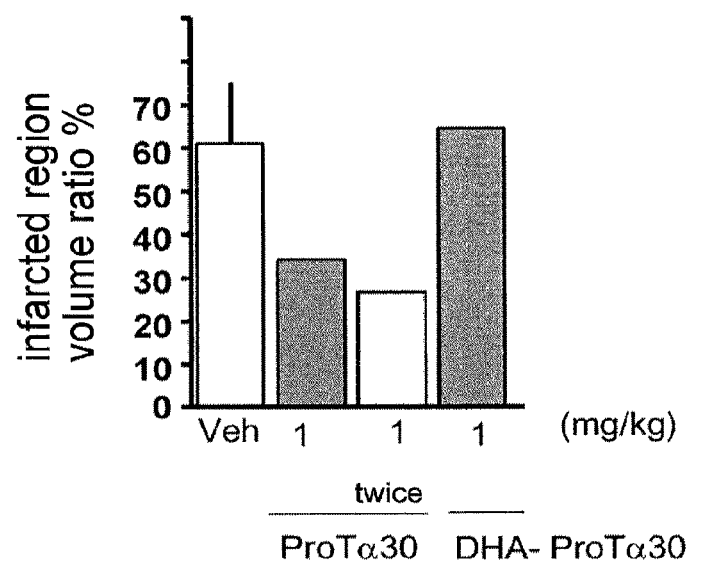

AGENT FOR AMELIORATING BLOOD-BRAIN BARRIER DISORDERS

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 42,347 bytes ASCII (Text) file named "709835Replacement-SequenceListing," created Jul. 17, 2014.

TECHNICAL FIELD

The present invention relates to a blood-brain barrier disorder ameliorator and a therapeutic agent for a disease accompanied by a blood-brain barrier disorder, each containing a prothymosin α-derived polypeptide or the like as an active ingredient, and the like.

BACKGROUND ART

In the human brain, several ten billion nerve cells constitute a complex network; however, if the mechanism for neurogenesis from a few nerve stem cells is not taken into account, the cell count basically continues to decrease after birth. During the long lifespan reportedly extending to hundred and several tens of years, the brain works to maintain survival by making the best use of a variety of protective mechanisms against a variety of extraneous and endogenous stresses. In the protective mechanisms possessed by the brain itself, nerve-glia and nerve-nerve communities are working while influencing each other to maintain their sophisticated roles. The best known nerve protecting mechanism is functionalized by molecules such as neurotrophic factors and cytokines. These neurotrophic factors are known to have the function of suppressing programmed nerve cell death (apoptosis), which is seen under a variety of stress conditions. Another mechanism is neurogenesis; although it has recently been reported that neurogenesis is accentuated under cerebral ischemic stress, which, however, is expected to be insufficient to compensate for large amounts of nerves undergoing cell death.

During cerebral ischemia, necrosis, which is destructive cell death, is observed in the core portion at the center of ischemia; because this cell death involves the discharge of cell content to the outside, the cytotoxic action should essentially further diffuse to the surroundings. Several days later, however, apoptosis-specific phenomena, such as cell fragmentation, condensation, and phagocytosis by microglia and the like, are observed in the surrounding region known as the penumbra. This apoptosis seen in the penumbra is thought to function as a kind of protective mechanism that prevents the entire brain from being injured, by localizing the injured site (see Non-patent Document 1). The present inventor found for the first time that the above-described conversion of the form of cell death from necrosis to apoptosis observed during cerebral ischemia is caused by prothymosin α (see Non-patent Document 2).

By the way, cerebral stroke is an important disease ranking the third in mortality rate and the first as an etiology of bed-ridden state among Japanese, being a disease developing as a result of cerebral ischemia. In cerebral stroke, treatment in the acute stage is said to be important in the meaning of improving the prognosis. A major therapeutic method that is currently drawing attention involves thrombolytic agents, including plasminogen activators (hereinafter denoted as "tPA"); the use thereof is limited to within 3 hours, patients that can enjoy the benefit accounting for only about ten-odd percent (see Non-patent Document 3). This is because the blood-brain barrier embrittles with elapse of time after cerebral stroke, and hence because the risk of hemorrhagic cerebral stroke increases with use of thrombolytic agents such as tPA. However, no substance possessing the action of protecting the blood-brain barrier against the embrittlement of the blood-brain barrier that can be used along with thrombolytic agents has been found yet.

The present inventor recently found for the first time that prothymosin α is a substance possessing protecting action against nerve cell death, and capable of mitigating cerebral stroke disorders by this nerve cell death suppressing effect (see Patent Document 1). The present inventor and others also found that prothymosin α has the effect of suppressing cerebral stroke and ischemic glaucoma in mice and rats (see Non-patent Documents 4-6).

PRIOR ART DOCUMENT

Patent Document

Patent Document 1: WO2004/064861

Non-patent Document

Non-patent Document 1: Hiroshi Ueda, Wakako Hamanabe, Folia Pharmacologica Japonica, 119, 79-88 (2002)
Non-patent Document 2: Medical Bio, March 2008, pp. 83-89
Non-patent Document 3: Modern Medical Care: Medical care: Medical care and nursing: Yomiuri Shimbun Online, article dated Oct. 25, 2005, "New medicine tPA for cerebral infarction", http://www.yomiuri.co.jp/iryou/medi/saisin/20051025ik14.htm
Non-patent Document 4: Journal of Cell Biology (2007), 176, 853-862
Non-patent Document 5: Cell Death and Differentiation (2007), 14, 1839-1842
Non-patent Document 6: Cell Death and Differentiation (2009), 16, 349-358

SUMMARY OF THE INVENTION

Problems to be Solved by the Invention

There is a demand for a substance capable of suppressing the embrittlement of the blood-brain barrier that can occur due to cerebral ischemia to protect the blood-brain barrier.

Means of Solving the Problems

The present inventor conducted extensive investigations to solve the above-described problems and, as a result, found that prothymosin α possesses the function of remarkably suppressing blood-brain barrier embrittlement that develops due to cerebral ischemia, separately from the conventionally known protecting action against nerve cell death. Considering the facts that prothymosin α has been confirmed to transfer into the brain during ischemia and functions as a nerve protecting substance by suppressing nerve cell death, the present inventor extensively investigated, and have developed the present invention.

Accordingly, the present invention relates to:
[1] a blood-brain barrier disorder ameliorator comprising, as an active ingredient, a prothymosin α-derived polypeptide or a polypeptide possessing substantially the same function as said prothymosin α-derived polypeptide;

[2] the agent described in [1], wherein the prothymosin α-derived polypeptide comprises a polypeptide shown by an amino acid sequence selected from among SEQ ID NO:4 to 6;

[3] a therapeutic agent for a disease accompanied by a blood-brain barrier disorder, comprising, as an active ingredient, a prothymosin α-derived polypeptide or a polypeptide possessing substantially the same function as said prothymosin α-derived polypeptide;

[4] the agent described in [3], wherein the prothymosin α-derived polypeptide comprises a polypeptide shown by an amino acid sequence selected from among SEQ ID NO:4 to 6;

[5] the agent described in [3] or [4], wherein the disease accompanied by a blood-brain barrier disorder is a secondary vasculopathy due to atherosclerosis or hypertension, transient blood flow disturbance, hypertensive encephalopathy, intra/extracranial arterial embolism, infarction resulting from thrombosis, aneurysm, arteriovenous malformation, cerebral artery stenotic lesion, dural arteriovenous fistula, vascular trauma, vascular tumor, viral infectious encephalitis, or edema or hemorrhagic disease due to vulnerable vascularization after cerebral infarction;

[6] a therapeutic agent for a cerebral ischemic disease, comprising, as active ingredients, a prothymosin α-derived polypeptide or a polypeptide possessing substantially the same function as said prothymosin α-derived polypeptide, as well as a thrombolytic ingredient;

[7] the therapeutic agent described in [6], wherein the prothymosin α-derived polypeptide comprises a polypeptide shown by an amino acid sequence selected from among SEQ ID NO:4 to 6;

[8] the therapeutic agent described in [6] or [7], wherein the thrombolytic ingredient is a plasminogen activator,

[9] the therapeutic agent described in any one of [6] to [8], wherein the cerebral ischemic disease is cerebral infarction;

[10] a polypeptide comprising an amino acid sequence selected from among SEQ ID NO:4 to 6;

[11] a use of a prothymosin α-derived polypeptide or a polypeptide possessing substantially the same function as said prothymosin α-derived polypeptide, for producing a blood-brain barrier disorder ameliorator;

[12] the use described in [11], wherein the prothymosin α-derived polypeptide comprises a polypeptide shown by an amino acid sequence selected from among SEQ ID NO:4 to 6; and the like.

Effect of the Invention

The blood-brain barrier disorder ameliorator of the present invention is capable of ameliorating the embrittlement of the blood-brain barrier that can occur due to cerebral ischemia. Therefore, the agent of the present invention can be a therapeutic agent for a disease resulting from a blood-brain barrier disorder.

The blood-brain barrier disorder ameliorator of the present invention is useful in the prevention and treatment of diseases accompanied by blood-brain barrier disorders, i.e., secondary vasculopathies due to atherosclerosis or hypertension, transient blood flow disturbance, hypertensive encephalopathy, intra/extracranial arterial embolism, infarction resulting from thrombosis, aneurysms, arteriovenous malformations, cerebral artery stenotic lesions, dural arteriovenous fistulas, vascular traumas, vascular tumors, viral infectious encephalitis, and edema or hemorrhagic diseases due to vulnerable vascularization after cerebral infarction.

Even in cases where thrombolytic agents are judged to be conventionally inapplicable in the case of embrittlement of the blood-brain barrier due to cerebral ischemia, by using a thrombolytic agent in combination with the agent of the present invention, a cerebral ischemic disease can be treated without worrying about adverse reactions such as cerebral hemorrhage due to the thrombolytic agent.

BRIEF DESCRIPTION OF THE DRAWINGS

FIG. 1-1 is a drawing showing the amino acid sequences of prothymosin α actually obtained from organisms such as humans, rats, and mice (the right ends of the amino acid sequences in FIG. 1-1 and the left ends of the amino acid sequences in FIG. 1-2 link each other, and the right ends of the amino acid sequences in FIG. 1-2 and the left ends of the amino acid sequences in FIG. 1-3 link each other).

FIG. 1-2 is a drawing showing the amino acid sequences of prothymosin α actually obtained from organisms such as humans, rats, and mice (the right ends of the amino acid sequences in FIG. 1-1 and the left ends of the amino acid sequences in FIG. 1-2 link each other, and the right ends of the amino acid sequences in FIG. 1-2 and the left ends of the amino acid sequences in FIG. 1-3 link each other).

FIG. 1-3 is a drawing showing the amino acid sequences of prothymosin α actually obtained from organisms such as humans, rats, and mice (the right ends of the amino acid sequences in FIG. 1-1 and the left ends of the amino acid sequences in FIG. 1-2 link each other, and the right ends of the amino acid sequences in FIG. 1-2 and the left ends of the amino acid sequences in FIG. 1-3 link each other).

Figure 4:
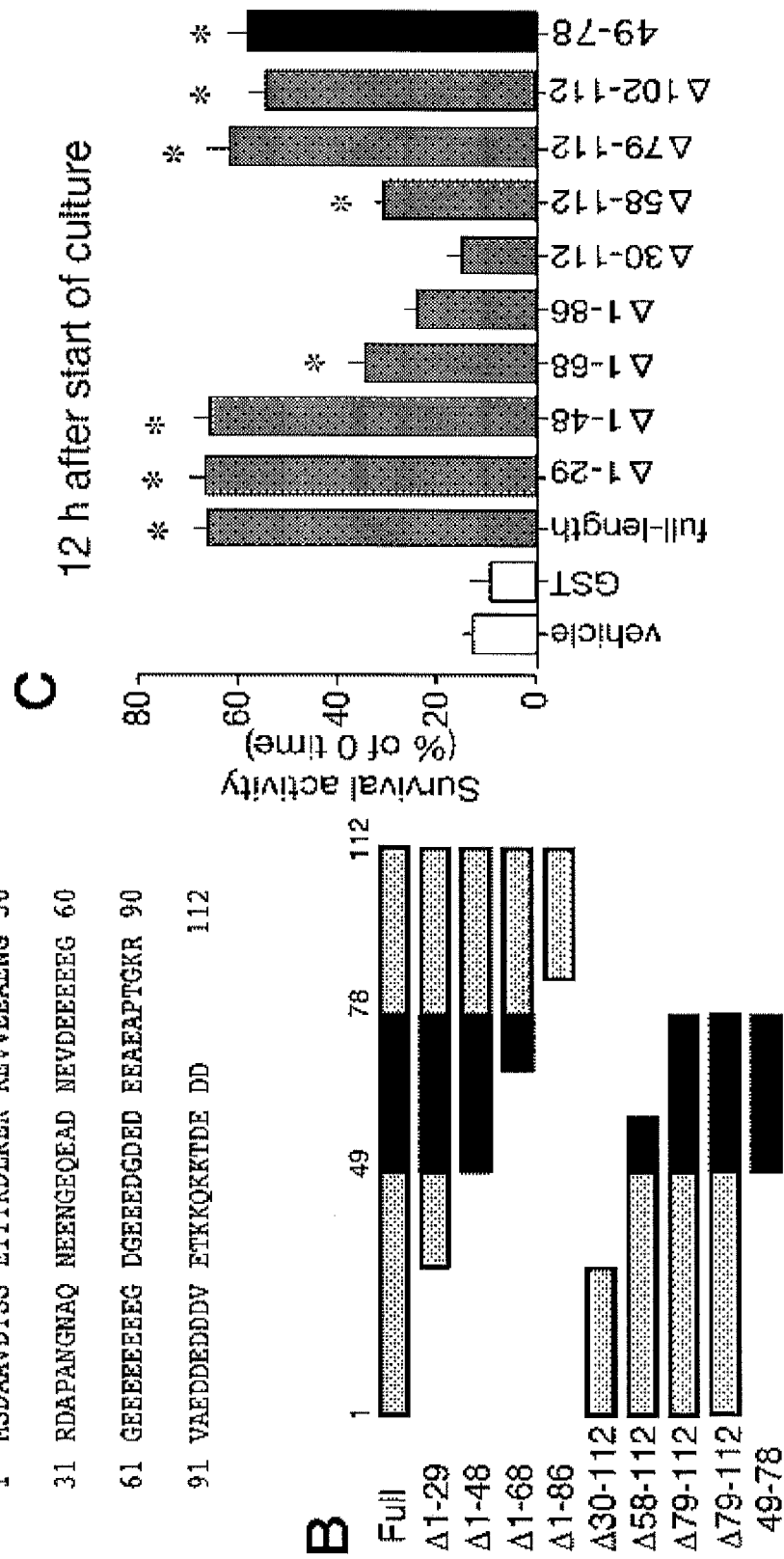

The amino acid sequences of FIGS. 1-1, 1-2, and 1-3 correspond to the following sequence identifiers: human 1 (SEQ ID NO: 7), human 2 (SEQ ID NO: 8), human 3 (SEQ ID NO: 9), human 4 (SEQ ID NO: 10), human 5 (SEQ ID NO: 11), human 6 (SEQ ID NO: 12), human 7 (SEQ ID NO: 13), human 8 (SEQ ID NO: 14), human 9 (SEQ ID NO: 15), human 10 (SEQ ID NO: 16), human 11 (SEQ ID NO: 17), human 12 (SEQ ID NO: 18), human 13 (SEQ ID NO: 19), human 14 (SEQ ID NO: 20), human 15 (SEQ ID NO: 21), human 16 (SEQ ID NO: 22), human 17 (SEQ ID NO: 23), human 18 (SEQ ID NO: 24), human 19 (SEQ ID NO: 25), human 20 (SEQ ID NO: 26), human 21 (SEQ ID NO: 27), human 22 (SEQ ID NO: 28), human 23 (SEQ ID NO: 29), rat1 (SEQ ID NO: 30), rat2 (SEQ ID NO: 31), rat3 (SEQ ID NO: 32), rat4 (SEQ ID NO: 33), rat5 (SEQ ID NO: 34), rat6 (SEQ ID NO: 35), rat7 (SEQ ID NO: 36), mouse1 (SEQ ID NO: 37), mouse2 (SEQ ID NO: 38), mouse3 (SEQ ID NO: 39), mouse4 (SEQ ID NOs: 40 and 41, respectively), zebrafish (SEQ ID NO: 42), and edible frog (SEQ ID NO: 43).

FIG. 2 is a drawing showing the amino acid sequences of human-, rat-, and mouse-derived prothymosin α. The amino acid sequences of FIG. 2 correspond to the following sequence identifiers: human-derived prothymosin α (SEQ ID NO: 1), rat-derived prothymosin α (SEQ ID NO: 3), mouse-derived prothymosin α (SEQ ID NO: 2), and thymosin (SEQ ID NO: 44).

FIG. 3 is a drawing showing the suppressing effects of prothymosin α on blood-brain barrier disorders. Contra shows the results obtained without infarction (contralateral-to-ischemia side); ipsi shows the results obtained with infarction (ipsilateral-to-ischemia side). Veh shows the results obtained with a vehicle, and ProTα shows the results obtained with prothymosin α. Each scale bar is 100 µm (×20 objective lens).

FIG. 4 is a drawing examining the cortical neuron survival activity of a prothymosin α-derived polypeptide for the purpose of searching for the active site of prothymosin α. In the drawing, Δ1-29, for example, indicates a polypeptide resulting from deleting the 1st to 29th amino acids from rat prothymosin α of 112 amino acid residues. The amino acid sequence of rat prothymosin alpha (rPROTα) in FIG. 4 corresponds to SEQ ID NO: 3.

Figure 5:
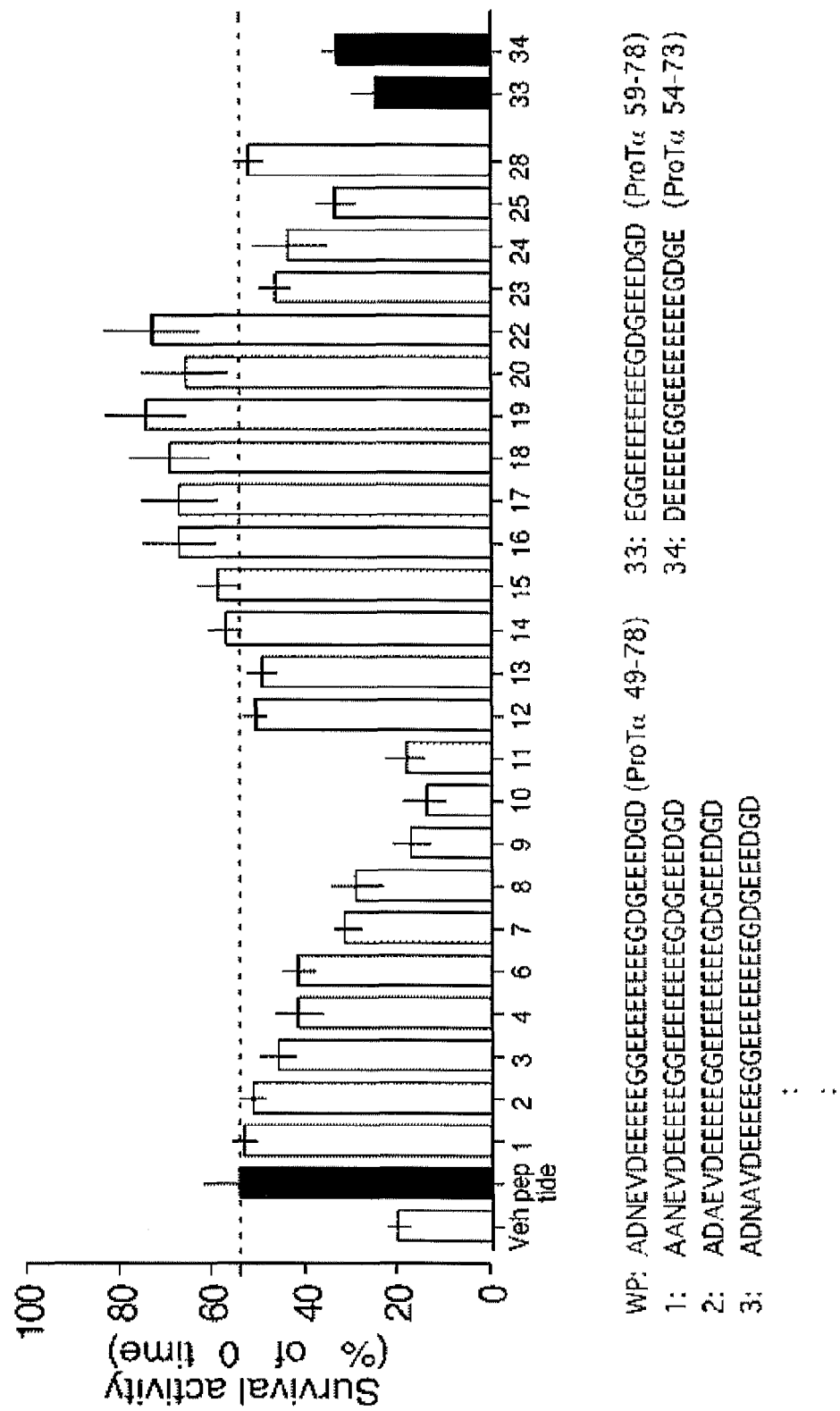

FIG. 5 is a drawing showing the results of alanine scanning of a polypeptide consisting of the 49th amino acid to the 78th amino acid of rat prothymosin α (ProTα30) with cortical neuron survival activity as an index. The amino acid sequences of FIG. 25 correspond to the following sequence identifiers: WP (SEQ ID NO: 4), 1 (SEQ ID NO: 45), 2 (SEQ ID NO: 46), 3 (SEQ ID NO: 47), 33 (SEQ ID NO: 48), and 34 (SEQ ID NO: 49).

Figure 6:
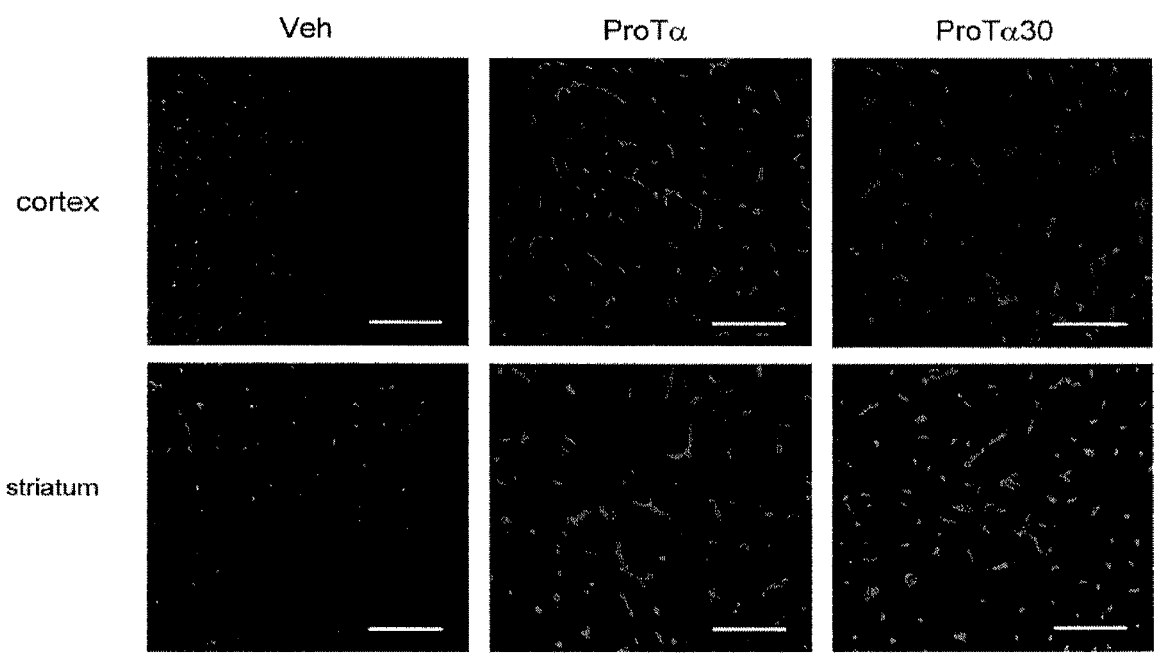

FIG. 6 is a drawing showing the suppressing effect of ProTα30 on blood-brain barrier disorders. Cortex shows the results for cerebral cortex: Striatum shows the results for striatum. Each scale bar is 100 μm (×20 objective lens).

FIG. 7 is a drawing showing the results of an evaluation of survival rate and movement disorders in C57BL/J6 mice with cerebral ischemia transiently induced by infarcting the left middle cerebral artery, receiving ProTα30 administered intracerebroventricularly. Movement disorders subsequent to left middle cerebral artery infarction are rated using the clinical scores 1 to 5 shown below. 1: unable to completely extend the right forelimb, 2: rightward turning behavior, 3: unable to keep the posture and leans in the rightward direction, 4: loss of spontaneous movement, 5: death FIG. 8 is a drawing showing the results of an evaluation of infarction region volume in C57BL/J6 mice with cerebral ischemia transiently induced by infarcting the left middle cerebral artery, receiving ProTα30 administered intracerebroventricularly.

FIG. 9 is a drawing showing the results of an evaluation of infarction region volume and motor function in C57BL/J6 mice with cerebral ischemia transiently induced by infarcting the left middle cerebral artery, receiving varied doses of ProTα30 administered into a caudal vein. DHA-ProTα30 represents ProTα30 modified with docosahexaenoic acid at the N end. Clinical scores are as defined in FIG. 7. * indicates a significant difference.

FIG. 10 is a drawing showing the results of an evaluation of infarction region volume in C57BL/J6 mice with cerebral ischemia permanently induced by infarcting the left middle cerebral artery, receiving ProTα30 administered a plurality of times into a caudal vein.

Figure 11:
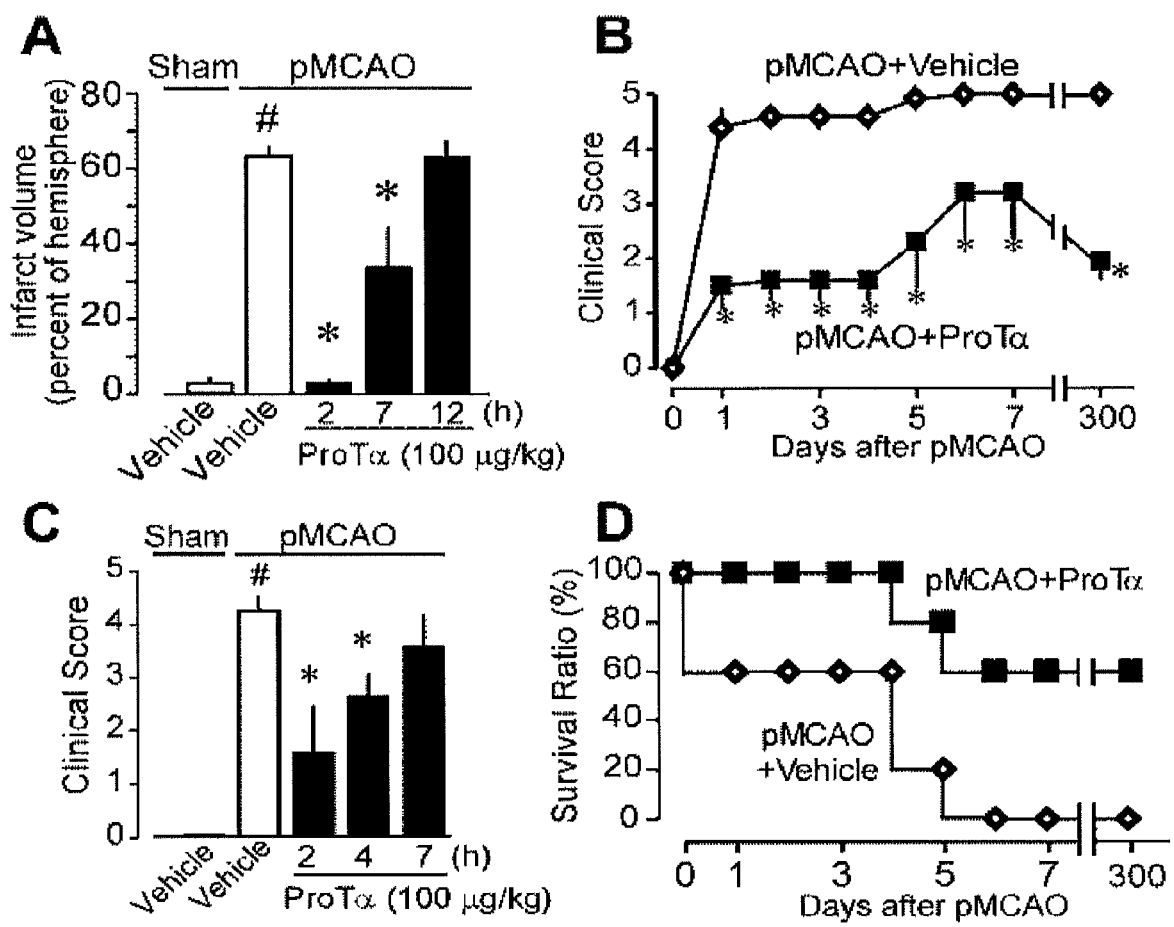

FIG. 11 is a drawing showing the results of an evaluation of infarction region volume, survival rate and movement disorders in C57BL/J6 mice with cerebral ischemia permanently induced by infarcting the left middle cerebral artery, receiving ProTα administered into a caudal vein. Clinical scores are as defined in FIG. 7. pMCAO represents a permanent cerebral ischemia group. Sham represents a sham surgery control group. * indicates a significant difference ($P<0.05$, vs. Vehicle); # indicates a significant difference ($P<0.05$, vs. Sham).

Figure 12:
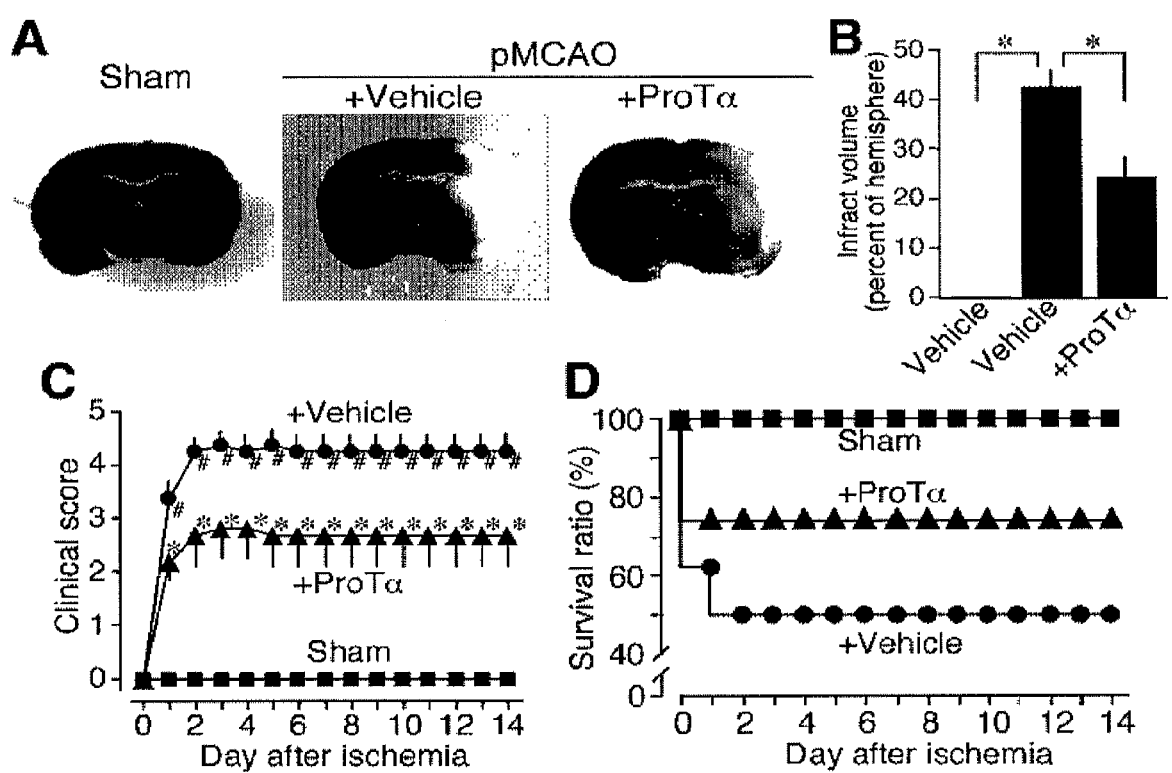

FIG. 12 is a drawing showing the results of an evaluation of infarction region volume, survival rate and movement disorders in Sprague-Dawley rats with cerebral ischemia permanently induced by infarcting the left middle cerebral artery, receiving ProTα administered into a caudal vein. Clinical scores are as defined in FIG. 7. pMCAO represents a permanent cerebral ischemia group. Sham represents a sham surgery control group. * indicates a significant difference ($P<0.05$, vs. Sham); # indicates a significant difference ($P<0.05$, vs. pMCAO-Vehicle).

Figure 13:
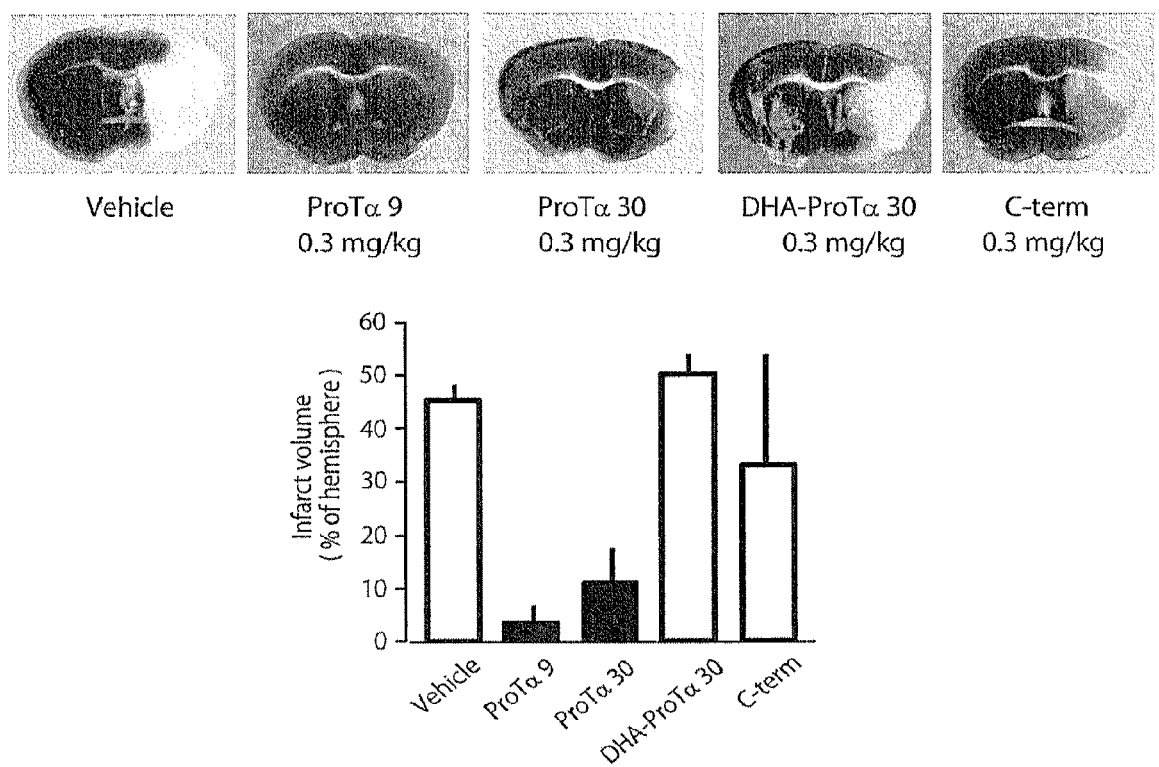

FIG. 13 is a drawing showing the results of a comparison of infarction region volume in C57BL/J6 mice with cerebral ischemia transiently induced by infarcting the left middle cerebral artery, obtained with administration of a polypeptide consisting of the 52nd amino acid to the 60th amino acid of rat prothymosin α (ProTα9) into a caudal vein, compared with administration of other polypeptides. DHA-ProTα30 represents ProTα30 modified with docosahexaenoic acid at the N end. C-term represents the C-end of ProTα.

Figure 14:
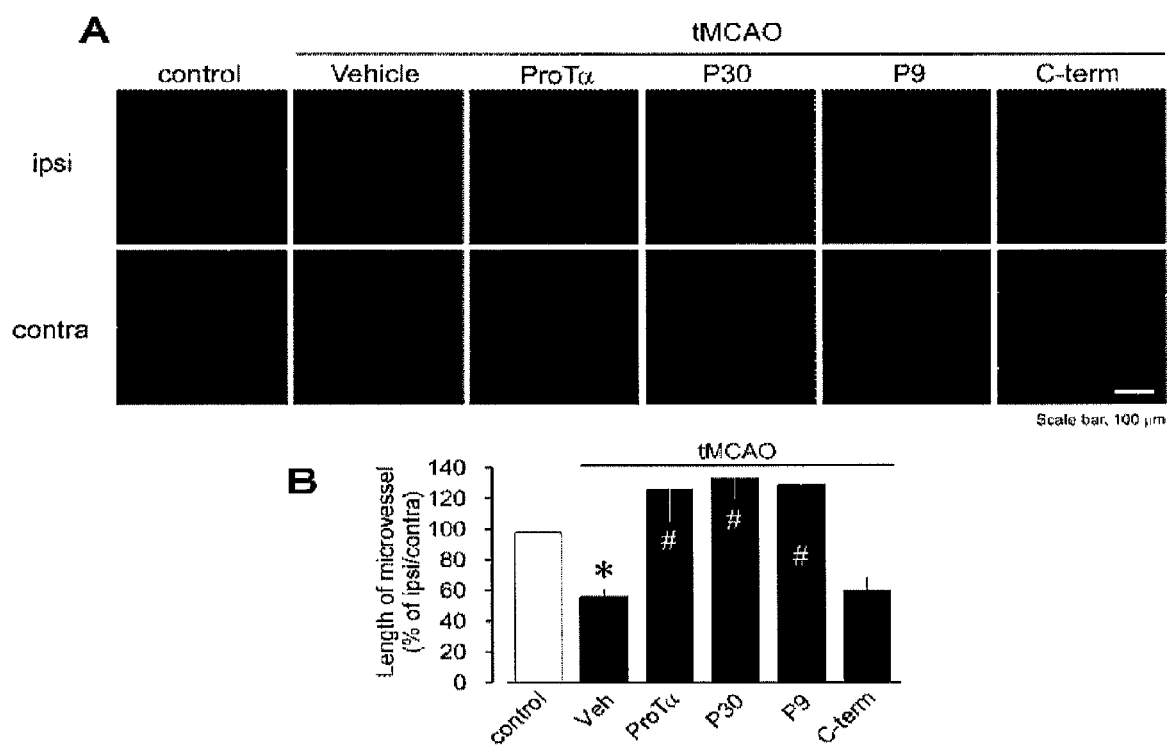

FIG. 14 is a drawing showing the suppressing effect of ProTα9 on blood-brain barrier disorders. A represents tomato lectin staining of microvessels; B is a bar graph of mean values of microvessel length represented by A. tMCAO represents a transient cerebral ischemia group. * indicates a significant difference ($P<0.05$, vs. without-tMCAO Control), # indicates a significant difference ($P<0.05$, vs. tMCAO Veh). The scale bar in A is 100 μm (×20 objective lens).

Figure 15:
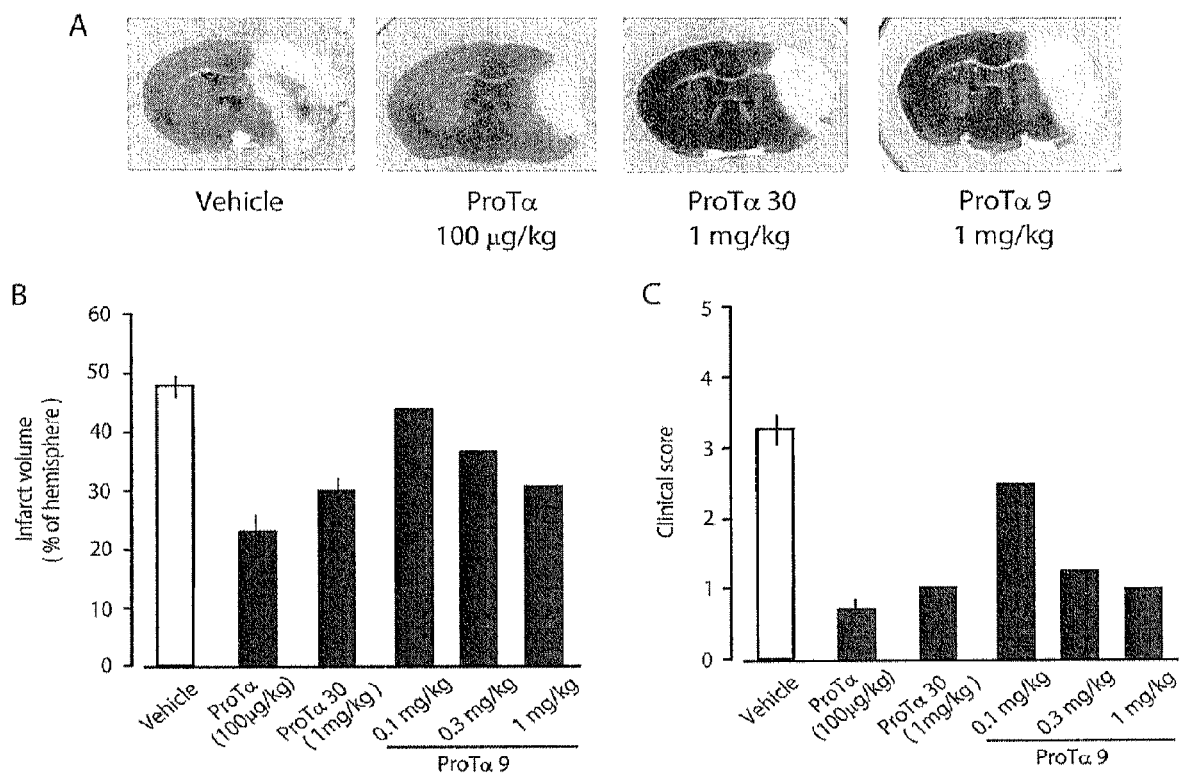

FIG. 15 is a drawing showing the results of an evaluation of infarction region volume and clinical scores in photoinduced middle cerebral artery thrombosis (PIT) model mice receiving ProTα9 and the like administered into a caudal vein. Clinical scores are as defined in FIG. 7.

MODES FOR EMBODYING THE INVENTION

The present invention is hereinafter described in detail.

Prothymosin α (hereinafter sometimes denoted as "ProTα") is a known protein, and has conventionally been known to possess the function of protecting against nerve cell death and the function of suppressing nerve cell death. However, the present invention has been developed on the basis of the discovery of a separate function of the action of ProTα, i.e., "the function of remarkably suppressing cerebral ischemic blood-brain barrier embrittlement to ameliorate blood-brain barrier disorders".

The "function of suppressing cerebral ischemic blood-brain barrier embrittlement" and "the function of ameliorating blood-brain barrier disorders" of ProTα were found for the first time by the present inventor.

The blood-brain barrier is a mechanism that controls material exchange between the blood and the brain tissue fluid. The mechanism for material exchange control by the blood-brain barrier is supported by positive mechanisms, including the intracerebral uptake of essential endogenous substances serving as nervous activity energy sources, including amino acids and glucose, and discharge of intracerebral toxins, unwanted foreign matter and the like in the blood. The mechanisms can be controlled by many transport systems by transporter expressed in cerebral capillary endothelial cells. When anatomically viewing the blood-brain barrier, it is seen that the cerebral capillary endothelial cells constituting the blood-brain barrier form tight junctions to restrict the permeability of intercellular spaces. That is, thanks to the presence of the blood-brain barrier, the biochemical homeostasis of the central nervous system is maintained at high levels. Therefore, if an abnormality occurs in the blood-brain barrier, abnormalities occur in the cerebrovascular and intracerebral selective substance permeability, which abnormalities result in an impact on the central nervous system.

During cerebral infarction, ischemic symptoms develop not only in the infarcted site, but also in the blood-brain barrier. Because the blood vessels in the portion where ischemic symptoms have developed weaken abruptly, the probability of bleeding from the blood-brain barrier is extremely high when blood flows are restored. Therefore, thrombolytic agents that are useful in cerebral infarction treatment are mostly inapplicable because they cannot be used unless the pathologic condition is identified within 6 hours (preferably 3 hours) after infarction. The ProTα used in the present invention is used for the purpose of ameliorating the embrittleness of the blood-brain barrier so that thrombolytic agents can be applied even in such situations.

"A blood-brain barrier disorder" in the present invention refers to any abnormality developing in the blood-brain barrier. Such abnormalities include abnormalities in the selective permeability of substances in the blood-brain barrier, collapse of tight junctions of cerebral capillary endothelial cells (expansion of intercellular spaces), cerebral capillary endothelial cell reductions and accompanying fever, and encephalitic symptoms such as cerebral edema, as well as absolutely all higher cerebral functional disorders such as memory/learning, appetite, and sleep disturbances and emotional pain, and autonomic nervous diseases accompanied by blood pressure, respiratory, and gastrointestinal symptoms and the like. The blood-brain barrier disorder ameliorator of the present invention ameliorates such abnormalities in the blood-brain barrier to restore the function of the blood-brain barrier.

An abnormality in the blood-brain barrier can specifically be identified by, for example, the number/quantity and length of capillaries in the cerebrocortical sensation region. That is, if the capillaries in the cerebrocortical sensation region are scarce, it can be judged that an abnormality in the blood-brain barrier has occurred as a result of cerebral infarction; if the capillaries in the cerebrocortical sensation region are available in appropriate amounts, it can be judged that there is no abnormality in the blood-brain barrier. The length and quantity of capillaries can be determined by methods known per se; such methods include the staining of vascular endothelial cells with lectins (e.g., tomato lectin) described in "Seitai no Kagaku; Vol. 55(3), pp. 266-272 (by Shunichi Morikawa and Taichi Ezaki), 2004".

Judging from the findings shown above, prothymosin α can be utilized as a blood-brain barrier disorder ameliorator. The prothymosin α used in the blood-brain barrier disorder ameliorator is not particularly limited; human-derived prothymosin α, rat-derived prothymosin α, mouse-derived prothymosin α and the like, irrespective of the animal species, can also be used. Comparisons of the amino acid sequences of prothymosin α actually obtained from tissues of these animal species are shown in FIG. 1-1 to FIG. 1-3. The right ends of the amino acid sequences in FIG. 1-1 and the left ends of the amino acid sequences in FIG. 1-2 link each other, and the right ends of the amino acid sequences in FIGS. 1-2 and the left ends of the amino acid sequences in FIG. 1-3 link each other.

Also, with the amino acid sequences of three kinds of prothymosin α, in particular, out of these prothymosin α, shown by SEQ ID NO:1 (human-derived), SEQ ID NO:2 (mouse-derived), and SEQ ID NO:3 (rat-derived), comparisons of these sequences in due order are shown in FIG. 2. As prothymosin α derived from an animal species other than humans, rats, and mice, bovine-derived prothymosin α, frog-derived prothymosin α and the like can also be used. The amino acid sequences of these prothymosin α are registered with GenBank and the like under Accession Nos. TNBOA1 and CAC39397, respectively.

In place of prothymosin α, a prothymosin α-derived polypeptide or a polypeptide possessing substantially the same function as said prothymosin α-derived polypeptide can also be used. Here, "a prothymosin α-derived polypeptide" or "a polypeptide possessing substantially the same function as said prothymosin α-derived polypeptide" is a polypeptide having the function possessed by prothymosin α, for example, the functions of protecting against blood-brain barrier disorders and ameliorating the same (e.g., GLUT4 cell membrane surface localization promoting action and the like), functions of protecting against nerve cell death/nerve cell death suppressing functions (e.g., necrosis suppressing function, apoptosis promoting function, indirect apoptosis suppressing function and the like).

The "prothymosin α-derived polypeptide" is not particularly limited, as far as the polypeptide has the same amino acid sequence as a portion or all of the above-described full-length amino acid sequence of prothymosin α, and possesses the function possessed by prothymosin α, for example, the functions of protecting against blood-brain barrier disorders and ameliorating the same (e.g., GLUT4 cell membrane surface localization promoting action and the like), functions of protecting against nerve cell death/nerve cell death suppressing functions (e.g., necrosis suppressing function, apoptosis promoting function, indirect apoptosis suppressing function and the like) and the like.

Such polypeptides include, for example, the polypeptide shown by the amino acid sequence of SEQ ID NO:1, the polypeptide shown by the amino acid sequence of SEQ ID NO:2, the polypeptide shown by the amino acid sequence of SEQ ID NO:3 (see FIG. 2), or polypeptides comprising these polypeptides.

Meanwhile, it is desirable that these polypeptides be further shortened for the purpose of applying to drug discovery seeds. The length of the polypeptide (degree of shortening) is not particularly limited, as far as it retains the above-described function possessed by prothymosin α and is applicable as a drug discovery seed; such polypeptides suitably include polypeptides of 30 amino acids or less, specifically including, for example, the polypeptide shown by the amino acid sequence of SEQ ID NO:4, the polypeptide shown by the amino acid sequence of SEQ ID NO:5, the polypeptide shown by the amino acid sequence of SEQ ID NO:6 and/or polypeptides comprising these polypeptides.

These polypeptides can also be preferably used as active ingredients for the blood-brain barrier improver, therapeutic agent for a disease accompanied by a blood-brain barrier disorder, and therapeutic agent for a cerebral ischemic disease, of the present invention described below.

The polypeptide shown by the amino acid sequence of SEQ ID NO:4 is a polypeptide consisting of the 49th amino acid to the 78th amino acid of rat prothymosin α (herein sometimes denoted as "ProTα30"). ProTα30 is a polypeptide possessing the function as the active form of prothymosin α, as shown in Example 2 below.

Furthermore, the polypeptide shown by the amino acid sequence of SEQ ID NO:6 is a polypeptide consisting of the 52nd amino acid to the 60th amino acid of rat prothymosin α (herein sometimes denoted as "ProTα9"). ProTα9 is a portion more important to the activity of prothymosin α in ProTα30, as shown in Example 3 below.

These polypeptides or polypeptides comprising these polypeptides possess the functions of protecting against blood-brain barrier disorders and ameliorating the same (e.g., GLUT4 cell membrane surface localization promoting action and the like), functions of protecting against nerve cell death/nerve cell death suppressing functions (e.g., necrosis suppressing function, apoptosis promoting function, indirect apoptosis suppressing function and the like) and the like, and can be preferably used as active ingredients for the blood-brain barrier improver, therapeutic agent for a disease accompanied by a blood-brain barrier disorder, and therapeutic agent for cerebral ischemic disease of the present invention described below.

"Polypeptides possessing substantially the same function as prothymosin α-derived polypeptides" include polypeptides having the same function possessed by prothymosin α as the above-described "prothymosin α-derived polypeptide", for example, the functions of protecting against blood-brain barrier disorders and ameliorating the same (e.g., GLUT4 cell membrane surface localization promoting action and the like), functions of protecting against nerve cell death/nerve cell death suppressing functions (e.g., necrosis suppressing function, apoptosis promoting function, indirect apoptosis suppressing function and the like) and the like and resulting from deletion, addition, substitution or translocation of one or a plurality of amino acids in the amino acid sequence of the "prothymosin α-derived polypeptide".

Here, the number of deleted, added, substituted or translocated amino acids is not particularly limited, as far as the same function as prothymosin α is possessed, and the number is normally within 20, preferably within 10, particularly preferably within 5, most preferably within 3.

The peptides shown by amino acid sequences corresponding to SEQ ID NO:4 in FIG. 1-1 to FIG. 1-3 (the amino acid sequences positioned in the same row as "the rat active form" in FIG. 1-1 to FIG. 1-3) are included in these "polypeptides possessing substantially the same function as prothymosin α-derived polypeptides".

These polypeptides can be produced by methods of peptide synthesis known per se. Deletion, addition, substitution or translocation of an amino acid can also be performed by a method known per se.

Furthermore, these polypeptides may be modified with peptides, as far as they have the same function possessed by prothymosin α as the above-described "prothymosin α-derived polypeptide", for example, the functions of protecting against blood-brain barrier disorders and ameliorating the same (e.g., GLUT4 cell membrane surface localization promoting action and the like), functions of protecting against nerve cell death/nerve cell death suppressing functions (e.g., necrosis suppressing function, apoptosis promoting function, indirect apoptosis suppressing function and the like) and the like.

Modifications of peptides include, for example, phosphorylation (e.g., Ser($PO_3H_2$), Thr($PO_3H_2$), Tyr($PO_3H_2$) and the like), sulfation (e.g., Tyr($SO_3H$) and the like), amino group modifications (e.g., acetylation, succinylation, biotinylation, Z conjugation, Dnp conjugation, Dns conjugation, myristoylation and the like), thiol group modifications (e.g., farnesylation, geranylation and the like), modifications with sugars (e.g., Asn(GlcNAc), Ser/Thr(GalNAc), Ser/Thr(Gal-Gal-NAc), Ser/Thr(GlcNAc), Ser(Xyl), Thr(Man)-containing peptide and the like), peptide bond modifications (e.g., reduction type, statin type and the like), fluorescent labels (e.g., FITC conjugation, Dns conjugation, Nma conjugation and the like), other labels (e.g., biotin label and the like), modifications with fatty acids (e.g., DHA modification and the like) and the like.

The blood-brain barrier disorder ameliorator of the present invention comprises "a prothymosin α-derived polypeptide" or "a polypeptide possessing substantially the same function as a prothymosin α-derived polypeptide" as an active ingredient, and is therefore capable of protecting the blood-brain barrier against embrittleness resulting from cerebral ischemia to ameliorate blood-brain barrier disorders. Therefore, the blood-brain barrier disorder ameliorator of the present invention is capable of protecting the blood-brain barrier by the nerve protecting action possessed thereby, and even ameliorating the blood-brain barrier that has embrittled due to cerebral vasculopathy, and is therefore useful in the prevention or treatment of cerebral ischemic diseases at large, particularly diseases accompanied by blood-brain barrier disorders.

"Diseases accompanied by blood-brain barrier disorders" in the present invention include diseases known to produce abnormalities in the blood-brain barrier at large (for example, diseases where the tight junction structure of the blood-brain barrier embrittles physically, diseases where substance transport through the blood-brain barrier becomes abnormal and the like), diseases resulting from development of abnormalities in the blood-brain barrier and the like. Such diseases are mostly diseases accompanied by cerebral ischemia, specifically including secondary vasculopathies due to atherosclerosis or hypertension, transient blood flow disturbances, hypertensive encephalopathy, intra/extracranial arterial embolism, infarction resulting from thrombosis, aneurysms, arteriovenous malformations, cerebral artery stenotic lesions, dural arteriovenous fistulas, vascular traumas, vascular tumors, viral infectious encephalitis, or edema or hemorrhagic disease due to vulnerable vascularization after cerebral infarction and the like, as well as cerebral stroke, traumatic encephalopathy, glaucoma, compression disorders in diabetic retinopathy or retinal detachment treatment and the like. As mentioned here, "treatment" includes not only cases where the disease is completely cured, but also cases where the condition is mitigated, cases where the aggravation of the condition is prevented, and the like.

The "blood-brain barrier disorder ameliorator" and "therapeutic agent for a disease accompanied by a blood-brain barrier disorder" of the present invention are prepared into pharmaceutical preparations by blending "a prothymosin α-derived polypeptide" or "a polypeptide possessing substantially the same function as a prothymosin α-derived polypeptide", or these two polypeptides with a pharmaceutically acceptable carrier or diluent according to a publicly known method. While the appropriate pharmaceutically acceptable carrier or diluent is not particularly limited; a carrier or diluent known per se can be applied, for example, those describes in Remington's Pharmaceutical Sciences and the like can be mentioned.

Regarding the administration of the "blood-brain barrier disorder ameliorator" and "therapeutic agent for a disease accompanied by a blood-brain barrier disorder" of the present invention, the administration dosage form is not particularly limited, and administration dosage forms known per se can be applied; however, it is preferable that the same be prepared as an injection for vascular administration or intracerebroventricular administration as with publicly known pharmaceuticals for the treatment of cerebral vasculopathy. More specifically speaking, "a prothymosin α-derived polypeptide" or "a polypeptide possessing substantially the same function as a prothymosin α-derived polypeptide" is dissolved in an appropriate solvent such as water, physiological saline, or isotonized buffer solution to yield an injection. In this operation, the same can be prepared with the addition of polyethylene glycol, glucose, a variety of amino acids, collagen, albumin, and the like as protectants. It is also possible to administer the polypeptide as embedded in inclusion bodies such as ribosome.

When "a prothymosin α-derived polypeptide" or "a polypeptide possessing substantially the same function as a prothymosin α-derived polypeptide" is used to treat the above-described diseases, the dose thereof as an active ingredient is not particularly limited, and can easily be determined as appropriate by the medicating physician and the like, although it varies depending on the subject's age, body weight, disease condition, route for administration, and other factors. For example, when the same is intracerebroventricularly administered to treat cerebral stroke, a daily dose of about 0.012 mg to 1.2 mg is administered; when the same is intravitreally administered for glaucoma treatment, a single dose of about 0.0012 mg to 0.012 mg is administered.

The method of administration of "a prothymosin α-derived polypeptide" or "a polypeptide possessing substantially the same function as a prothymosin α-derived polypeptide" is not particularly limited; a wide variety of methods of administration being in actual use can be employed. An example of such a method of administration is intracisternal administration. Intracisternal administration is advantageous in that brain parenchyma is not injured. The same may also be administered by non-oral administration (for example, intravascular administration (e.g., intravenous administration), intracerebroventricular administration and the like), oral administration and the like.

Also, the blood-brain barrier disorder ameliorator of the present invention, when used in combination with a thrombolytic agent, makes it possible to broaden the scope of application of the thrombolytic agent.

Generally, the application of thrombolytic agents is limited to patients within 3 hours after onset, in whom conventional vascular structures, including the blood-brain barrier, are retained in the acute stage of cerebral infarction, so that the agents are required to be used only after confirming the absence of intracranial hemorrhage by CT or MRI. This is because the blood-brain barrier embrittles due to cerebral ischemia, so that the risk of the development of adverse reactions such as bleeding due to the effect of the thrombolytic agent increases unless the structure of the blood-brain barrier in the initial stage of onset is relatively well maintained.

Hence, by using the blood-brain barrier disorder ameliorator of the present invention, the structure of the blood-brain barrier is maintained, so that there is no longer the concern about bleeding from embrittled blood vessels, which is a likely adverse reaction to the thrombolytic agent; therefore, a thrombolytic agent can be used without being influenced by the time of onset by using the agent of the present invention in combination. Thereby, it is possible to effectively treat cerebral ischemic diseases.

Accordingly, the present invention provides a therapeutic agent for cerebral ischemic disease comprising "a prothymosin α-derived polypeptide" or "a polypeptide possessing substantially the same function as a prothymosin α-derived polypeptide", and a thrombolytic ingredient as active ingredients.

Thrombolytic agents (thrombolytic ingredients) used in the present invention specifically include tPA, urokinase, streptokinase, natto kinase, prourokinase, staphylokinase, desmoteplase, APSAC and the like, or polypeptides derived from these thrombolytic ingredients. tPA is preferable. Here, "polypeptides derived from these thrombolytic ingredients" mean polypeptides possessing the activities possessed by the above-described thrombolytic ingredients, respectively, and having the same amino acid sequence as a portion or all of the full-length amino acid sequence of each thrombus-derived component (protein).

The tPA used may be a commercially available product or one synthesized by a method known per se.

The blood-brain barrier disorder ameliorator and therapeutic agent for cerebral ischemic disease of the present invention can be used in combination with another therapeutic agent for cerebral vasculopathy. The other therapeutic agent for cerebral vasculopathy is not particularly limited, as far as it is capable of treating cerebral vasculopathy; examples include, in addition to the above-described thrombolytic agents, radical scavengers (edaravone).

EXAMPLES

The present invention is hereinafter described in more detail by means of the following Examples.

Example 1

Suppressing Effect of Prothymosin α on Blood-Brain Barrier Disorders

Cerebral ischemia model mice generated by infarcting the left middle cerebral arteries of C57BL/J6 mice (male, weighing 21-26 g) were maintained for 0.5 or 1 hour, then reperfusion was performed. One hour after the reperfusion, a vehicle or ProTα (0.1 mg/kg) was intravenously administered (i.v.); further, 24 hours after the reperfusion, 50 mg/kg pentobarbital was intraperitoneally administered to perform general anesthesia, each treated mouse was allowed to stand on a bed being incubated at 37° C., and 100 µL of 1 mg/mL biotinylated tomato lectin (SIGMA, Lot number 048K3786) in solution in PBS was intravenously administered slowly over 2 to 3 minutes. Five minutes later, the whole body was perfused and fixed with para-formaldehyde (PFA); the brain was extracted and further treated with 4% PFA at room temperature for 3 hours. Thereafter, the brain was placed in 25% sucrose solution and allowed to stand at 4° C. overnight. The brain was freeze-embedded in the OCT compound, and a 50 µm-thick section was prepared on a plane including the cerebral cortex sensory area S1 (CS1) or S2 (CS2), bonded onto a silane-coated glass slide, and dried on a heater overnight. Thereafter, using Alexa Fluor488-labeled streptavidin (diluted 300 fold with 2% BSA/PBST), fluorescent staining of tomato lectin was performed, after which the specimen was fixed with the fluorescent antifading agent Fluoromount (Japan Tanner Corporation), and allowed to stand in the dark overnight, then examined using the LSM5 PASCAL confocal laser microscope (Carl Zeiss). Fluorescent signals were cumulatively analyzed for total fluorescence in an approximately 30 µm range by the deconvolution method.

After 0.5 hours of middle cerebral artery obstruction (MCAO), reperfusion was performed; 1 hour later, tomato lectin staining in the CS2 region was observed as a signal of approximately 30 µm length on the contralateral-to-ischemia side (the scale bar is 100 µm, ×20 objective lens). In contrast, on the ipsilateral-to-ischemia side, the signal was observed only as a fragment and was evaluable as cerebrovascular collapse. Even with 1 hour of MCAO reperfusion, the fluorescent signal was nearly equivalent, but time dependency was observed as an expansion of the brain region exhibiting vasculopathy (FIG. 3A).

In the mice receiving mouse recombinant ProTα (0.1 mg/kg) 1 hour after ischemia, the cerebrovascular destruction in the CS2 and striata on the ischemized side disappeared nearly completely (FIG. 3B).

Example 2

Search for the Active Form of Prothymosin α

With reference to the sequence of rat prothymosin α (FIG. 4A), the rat prothymosin α deletion variants shown in FIG. 4B were generated. Next, by applying the method of Ueda et al. (Ueda et al., J. Cell. Biol., 176, pp. 853-862, 2007), the active form of prothymosin α was searched for with the cortical neuron survival rate as an index.

Primary culture of nerve cells from cerebral cortex of a 17-day embryonic rat at $2\times10^4$ cells/cm$^2$ was started under serum-free conditions. Each deletion variant of rat prothymosin α, coupled with glutathione S-transferase (GST-ProTα fragment), at 100 nM was added starting at the initial stage of cultivation, and the cells were continued to be cultured in a 5% $CO_2$ incubator (37° C.) for 12 hours, after which surviving activity by WST-8 was evaluated.

As a result, a polypeptide consisting of 30 amino acids from the 49th alanine to the 78th aspartic acid (hereinafter sometimes denoted as "ProTα30") was identified as the active form of prothymosin α. The results are shown in FIG. 4C.

Example 3

Alanine Scanning of ProTα30

Variant peptides were generated by replacing each of the amino acid residues (30 residues) of the prothymosin α active form obtained in Example 1 with alanine one after another from the N end. Next, an evaluation was made to determine which region of the active form ProTα30 was associated with the expression of the activity by applying the method of Ueda et al. (Ueda et al., J. Cell. Biol., 176, pp. 853-862, 2007) with the cortical neuron survival rate as an index.

As a result, it was found that the EVDEEEEEG (SEQ ID NO:6) sequence, which corresponds to 52-60 in ProTα30, is a sequence important to the expression of the activity thereof. The results are shown in FIG. 5.

Example 4

Suppressing Effect of ProTα30 on Blood-Brain Barrier Disorders

The same experiment as that shown in Example 1 was performed using ProTα and the active form ProTα30, and the effects thereof were comparatively analyzed. The results are shown in FIG. 6.

As a result, ProTα30 was evaluated as suppressing cerebrovascular collapse, like ProTα. Thus, ProTα30 was also shown to have a suppressing effect on blood-brain barrier disorders.

Meanwhile, regarding efficacy, the conclusion that ProTα30 has a more potent suppressing effect on blood-brain barrier disorders than ProTα was not always reached; however, the size thereof proved to be promising in terms of cerebral transferability, economy, derivatizability and the like. ProTα30 also proved to possess the function of suppressing nerve cell death that can occur in the acute stage of cerebral ischemia (necrosis suppressing function).

Example 5

Effect of ProTα30 on Transient Cerebral Ischemia Model Mice (1)

Cerebral ischemia model mice generated by infarcting the left middle cerebral arteries of C57BL/J6 mice were maintained for 1 hour, and then reperfusion was performed. One hour after the reperfusion, a vehicle or ProTα30 (10 µg) was intracerebroventricularly administered (i.c.v.); the mice were examined over time every 24 hours to evaluate the motor function and survival rate. Also, clinical scores indicating movement disorders subsequent to left middle cerebral artery infarction were evaluated according to the rating system of 1: unable to completely extend the right forelimb, 2: rightward turning behavior, 3: unable to keep the posture and leans in the rightward direction, 4: loss of spontaneous movement, 5: death.

As a result, in the mice (n=4) receiving ProTα30 (10 µg) administered intracerebroventricularly 1 hour after ischemia and reperfusion, the survival rate, which reached a level for complete fatality 5 days after ischemia and reperfusion in the non-dosing group (n=4), improved to about 80% even 2 weeks later (FIG. 7A). In the motor function evaluation, it was proven that otherwise occurring loss of spontaneous movement 3 days after ischemia and reperfusion was significantly ameliorated by administration of ProTα30 (10 µg), although minor hemiparalysis remained (FIG. 7B).

Meanwhile, 1 hour after ischemia and reperfusion, ProTα30 (0 µg (Veh), 0.1 µg or 10 µg) was intracerebroventricularly administered; the whole brain, extracted 24 hours thereafter was treated with 2% TTC (2,3,5-Triphenyltetrazolium chloride) staining solution in solution in PBS, and washed with PBS, after which five coronary sections of 1 mm thickness were taken with coverage of 2 mm anteriorly and 3 mm posteriorly from the bregma. TTC staining is an index of cell survival activity based on the mitochondrial reducing reaction, in which non-disordered regions stain red, whereas disordered regions do not stain. Examined by this experiment was whether cerebral infarction was ameliorated by administration of ProTα30. The cerebral infarction region was evaluated according to the equation below. The portion that does not stain with TTC (red color) on the ischemized side appears to be clear in white, which portion is regarded as the infarction region on the ipsilateral side. All volume on the ipsilateral side refers to the entire infarcted and non-infarcted regions on the ischemized side as divided on the median line, whereas all volume on the contralateral side refers to the entire region on the non-ischemized side.

$$\text{Infarcted region volume ratio (\%)} = \frac{\text{All volume on contralateral side} - (\text{All volume on ipsilateral side} - \text{Infarcted region volume})}{\text{All volume on contralateral side}} \times 100 \quad \text{[Equation 1]}$$

As a result, in the samples with the solvent alone (n=7), 48% infarction was observed; infarction was suppressed in a dose-dependent fashion, to 44% with 0.1 µg of ProTα30 (n=2), and to 38% with 10 µg of ProTα30 (n=2) (FIG. 8A and FIG. 8B).

Example 6

Effect of ProTα30 on Transient Cerebral Ischemia Model Mice (2)

The same treatment as Example 5 was performed, and a vehicle, ProTα30 or ProTα30 modified with docosahexaenoic acid (DHA) at the N end (hereinafter denoted as "DHA-ProTα30") for the purpose of improving the cerebral transferability was intravenously administered (i.v.) at 1 mg/kg 1 hour after reperfusion. The results are shown in FIG. 9A, FIG. 9B and FIG. 9C.

As a result, in a control experiment with a solvent, 48% infarction was noted (n=7); however, when ProTα30 was once administered at 0.275 (n=3) and 1 mg/kg (n=3) 1 hour after reperfusion, the disorder was suppressed to 39% and 13% infarction, respectively, in a dose-dependent fashion. However, when DHA-ProTα30 was administered at 0.3 (n=2) and 1 mg/kg (n=3), no initially expected infarction region suppressing effect was noted (FIG. 9A, FIG. 9B).

Meanwhile, in an analysis of clinical scores, no effect was observed on hemiparalysis of degree 3 (n=11) with administration of ProTα30 at 0.275 mg/kg (i.v., n=4), but with administration of ProTα30 at 1 mg/kg (i.v., n=3), the same ameliorated significantly (FIG. 9C). A similar ameliorating effect was observed when DHA-ProTα30 was administered at 1 mg/kg (i.v., n=3), but not observed at 0.3 mg/kg (i.v., n=4). The finding that the DHA-derivatized peptide did not have a significant effect on the infarction region suggests the existence of unknown disordering action of this derivatization on ProTα.

Example 7

Effect of Multi-Dose Administration of ProTα30 on Permanent Cerebral Ischemia Model To permanent cerebral ischemia model mice generated by infarcting the middle cerebral arteries of C57BL/J6 mice, ProTα30 was intravenously administered (i.v.), without reperfusion, 2 hours and 4 hours after the start of ischemia. Next, 24 hours later, in the same manner as the above, infarction region volume was measured. The results are shown in FIG. 10A and FIG. 10B.

As a result, in a control experiment with a solvent, 60% infarction was noted (n=3); however, when ProTα30 was once administered (n=2) at 1 mg/kg (i.v) 2 hours after infarction; however, when the same was twice administered (n=1) at 2 hours and 4 hours, the disorder was suppressed to 34% and 27% infarction, respectively. However, when DHA-ProTα30 was once administered at 1 mg/kg (i.v., n=2), no initially expected infarction region suppressing effect was noted (FIGS. 10A and B).

Example 8

Effect of ProTα on Permanent Cerebral Ischemia Model Mice

To permanent cerebral ischemia model mice generated by infarcting the middle cerebral arteries of C57BL/J6 mice, ProTα was administered into a caudal vein at 100 μg/kg, without reperfusion, 2, 7, or 12 hours after the start of ischemia. Next, in the same manner as the above, infarction region volume was measured. As a result, in the permanent cerebral ischemia model mice as well, an infarction region suppressing effect was noted when the infarction lasted for a short time (FIG. 11A). In the same mice, motor function was evaluated. Clinical scores indicating motor function disorders were evaluated in the same manner as Example 5. As a result, it was found that even in the permanent cerebral ischemia model mice, motor function improved when the infarction lasted for a short time (FIG. 11C).

Meanwhile, a vehicle or ProTα (100 μg) was administered into a caudal vein (i.v.) 2 and 4 hours after the start of ischemia, and the mice were examined over time every 24 hours to evaluate the motor function and survival rate. As a result, in the mice (n=5) receiving ProTα (100 μg) administered into a caudal vein (i.v.), the survival rate, which reached a level for complete fatality 5 days after ischemia in the non-dosing group (n=5), improved to about 60% even about 2 weeks later (FIG. 11D). In the motor function evaluation, it was proven that otherwise occurring loss of spontaneous movement or death 1 day after ischemia was significantly ameliorated by administration of ProTα, although minor hemiparalysis remained (FIG. 11B).

Example 9

Effect of ProTα on Permanent Cerebral Ischemia Model Rats

To permanent cerebral ischemia model rats generated by infarcting the middle cerebral arteries of Sprague-Dawley rats, ProTα was administered into a caudal vein (i.v.), without reperfusion, 4 hours after the start of ischemia. Next, 24 hours later, infarction region volume was measured in the same manner as the above. The results are shown in FIG. 12A and FIG. 12B.

As a result, in the control experiment with a solvent (n=5), 40% infarction was noted; however, when ProTα was administered (n=5) at 100 μg/kg (i.v.) 4 hours after infarction, the disorder was suppressed to 25% infarction (FIGS. 12A and B).

Furthermore, rats were examined over time every 24 hours to evaluate the motor function and survival rate. As a result, in the rats (n=5) receiving ProTα (100 μg) administered into a caudal vein, the survival rate, which reached 50% one day after ischemia in the non-dosing group (n=5), improved to about 75% even about 2 weeks later (FIG. 12D). In the motor function evaluation, it was proven that otherwise occurring loss of spontaneous movement or death 2 days after ischemia and reperfusion ameliorated significantly with administration of ProTα, although minor hemiparalysis remained (FIG. 12C).

Example 10

Effect of ProTα9 on Transient Cerebral Ischemia Model Mice

Measurements of infarction region volume as in Example 5 were performed on transient cerebral ischemia model mice receiving ProTα9, the active form ProTα30, DHA-ProTα30 and the like administered at 0.3 mg/kg into a caudal vein (i.v.), and the effects of the polypeptides were comparatively analyzed. The results are shown in FIG. 13.

As a result, ProTα9, like ProTα30, was shown to have a cerebral infarction region suppressing effect against transient cerebral ischemia.

Example 11

Suppressing Effect of ProTα9 on Blood-Brain Barrier Disorders

Cerebral ischemia model mice generated by infarcting the left middle cerebral arteries of C57 BL/J6 mice were maintained for 1 hour, and then reperfusion was performed. One hour after the reperfusion, each of a vehicle, ProTα (100 μg/kg), ProTα30 (1 mg/kg), ProTα9 (0.3 mg/kg), and C-term (amino acid sequence TKKQKKTDEDD (SEQ ID NO: 50); 0.3 mg/kg) was administered into a caudal vein (i.v.). Furthermore, fluorescent staining of tomato lectin was performed in the same manner as in Example 1, and microvessels were analyzed. The results are shown in FIG. 14.

When reperfusion was performed after 1 hour of middle cerebral artery occlusion (MCAO), tomato lectin staining of the cerebrocortical sensation region was observed as a signal roughly 30 μm long on the contralateral-to-ischemia side (Contra). In contrast, on the ipsilateral-to-ischemia side (ipsi), signals with administration of Vehicle or C-term were observed only as a fragment, and was evaluable as cerebrovascular collapse (FIG. 14A).

Meanwhile, when ProTα, ProTα30 (P30), or ProTα9 (P9) was administered, longer signals were exhibited on the ipsilateral-to-ischemia side than on the contralateral-to-ischemia side (FIG. 14B). That is, ProTα9 was evaluable as having a cerebrovascular collapse suppressing effect, like ProTα30. Thus, ProTα9 was also proven to have a blood-brain barrier disorder suppressing effect.

Meanwhile, regarding efficacy, the conclusion that ProTα9 has a more potent suppressing effect on blood-brain barrier disorders than ProTα and ProTα30 was not always reached; however, the size thereof proved to be promising in terms of cerebral transferability, economy, derivatizability and the like.

Example 12

Effect of ProTα9 on Photoinduced Middle Cerebral Artery Thrombosis (PIT) Model Mice The left middle cerebral artery of a C57BL/J6 mouse was exposed under the dura, and the photosensitizing dye rose bengal was administered at 30 mg/kg into a caudal vein, after which green light with a given wavelength was irradiated to the middle cerebral artery for 10 minutes to produce a thrombus, and induce infarction with this thrombus. One hour after light irradiation, vehicle, ProTα (100 μg/kg), ProTα30 (1 mg/kg), or ProTα9 (0.1 mg/kg, 0.3 mg/kg and 1 mg/kg) was administered to a caudal vein. Next, after 24 hours of ischemia, infarction region volume was measured to evaluate the motor function in the same manner as the above. The results are shown in FIG. 15.

In a control experiment with a solvent, 48% infarction was noted (n=17); when ProTα was administered at 100 μg/kg 1 hour after infarction (n=6), the disorder was suppressed to 23% infarction; when ProTα30 was administered at 1 mg/kg (n=4), the disorder was suppressed to 30% infarction; when ProTα9 was administered (each dose n=2), the infarction injury region decreased in a dose-dependent fashion, the disorder being suppressed to 30% infarction by administration of 1 mg/kg (FIG. 15A, B). In the motor function evaluation, it was proven that the inability to keep the posture and leaning or the loss of spontaneous movement 24 hours after ischemia were significantly ameliorated by administration of ProTα, ProTα30 or ProTα9 (FIG. 15C).

The contents disclosed in any publication cited herein, including patents and patent applications, are hereby incorporated in their entireties by reference, to the extent that they have been disclosed herein.

INDUSTRIAL APPLICABILITY

The blood-brain barrier disorder ameliorator of the present invention is capable of ameliorating the embrittlement of the blood-brain barrier that can occur due to cerebral ischemia. Therefore, the agent of the present invention can be a therapeutic agent for a disease resulting from a blood-brain barrier disorder.

The present application is based on JP2009-185816 (filing date: Aug. 10, 2009) filed in Japan, the contents of which are encompassed in full herein.

[Sequence Listing Free Test]
Sequence No. 4 is a common amino acid sequence.
Sequence No. 6 is a common amino acid sequence.

The invention claimed is:

1. A method for ameliorating a blood-brain barrier disorder comprising administering by non-oral administration an effective amount of a polypeptide consisting of SEQ ID NO: 6 to a subject that has a blood-brain barrier disorder, thereby ameliorating the blood-brain barrier disorder in the subject.

2. The method according to claim 1, further comprising determining that capillary quantity and length in the cerebrocortical sensation region after administration of the effective amount of a polypeptide consisting of SEQ ID NO: 6.

3. The method according to claim 2, wherein the non-oral administration is intravascular administration, intracerebroventricular administration, or intracisternal administration.

4. A method for treating a disease accompanied by a blood-brain barrier disorder comprising administering by non-oral administration an effective amount of a polypeptide consisting of SEQ ID NO: 6 to a subject that has a disease accompanied by a blood-brain barrier disorder, thereby treating the disease accompanied by a blood-brain barrier disorder in the subject.

5. The method according to claim 4, wherein the disease accompanied by a blood-brain barrier disorder is selected from the group consisting of a secondary vasculopathy due to atherosclerosis or hypertension, transient blood flow disturbance, hypertensive encephalopathy, intra/extracranial arterial embolism, infarction resulting from thrombosis, aneurysm, arteriovenous malformation, cerebral artery stenotic lesion, dural arteriovenous fistula, vascular trauma, vascular tumor, viral infectious encephalitis, and edema or hemorrhagic disease due to vulnerable vascularization after cerebral infarction.

6. The method according to claim 4, further comprising determining capillary quantity and length in the cerebrocortical sensation region after administration of the effective amount of a polypeptide consisting of SEQ ID NO: 6.

7. The method according to claim 6, wherein the non-oral administration is intravascular administration, intracerebroventricular administration, or intracisternal administration.

8. A method for treating a cerebral ischemic disease comprising administering by non-oral administration an effective amount of a polypeptide consisting of SEQ ID NO: 6, as well as a thrombolytic ingredient, to a subject that has a cerebral ischemic disease, thereby treating the cerebral ischemic disease in the subject.

9. The method according to claim 8, wherein the thrombolytic ingredient is a plasminogen activator.

10. The method according to claim 9, wherein the cerebral ischemic disease is cerebral infarction.

11. The method according to claim 8, wherein the cerebral ischemic disease is cerebral infarction.

12. The method according to claim 8, further comprising determining that capillary quantity and length in the cerebrocortical sensation region after administration of the effective amount of a polypeptide consisting of SEQ ID NO: 6.

13. The method according to claim 12, wherein the non-oral administration is intravascular administration, intracerebroventricular administration, or intracisternal administration.

14. A method for treating cerebral stroke comprising administering intracerebroventricularly a daily dose of 0.012 mg to 1.2 mg of a polypeptide consisting of SEQ ID NO: 6 to a subject that has cerebral stroke, thereby treating cerebral stroke in the subject.

15. A method for treating glaucoma comprising administering intravitreally a daily dose of 0.0012 mg to 0.012 mg of a polypeptide consisting of SEQ ID NO: 6 to a subject that has glaucoma, thereby treating glaucoma in the subject.

* * * * *

```
                        SEQUENCE LISTING

<160> NUMBER OF SEQ ID NOS: 50

<210> SEQ ID NO 1
<211> LENGTH: 105
<212> TYPE: PRT
<213> ORGANISM: Homo sapiens

<400> SEQUENCE: 1

Met Ser Asp Ala Ala Val Asp Thr Ser Ser Glu Ile Thr Thr Glu Asp
1               5                   10                  15

Leu Lys Glu Lys Lys Glu Val Val Glu Glu Ala Glu Asn Gly Arg Asp
            20                  25                  30

Ala Pro Ala His Gly Asn Ala Asn Glu Glu Asn Gly Glu Pro Glu Ala
        35                  40                  45

Asp Asn Glu Val Asp Glu Glu Glu Glu Gly Gly Glu Glu Glu Glu Gly
    50                  55                  60

Asp Gly Glu Glu Glu Asp Gly Asp Glu Asp Glu Gly Ala Glu Ser Ala
65                  70                  75                  80

Thr Gly Lys Arg Ala Ala Glu Asp Asp Glu Asp Asp Asp Val Asp Thr
                85                  90                  95

Gln Lys Gln Lys Thr Asp Glu Asp Asp
            100                 105

<210> SEQ ID NO 2
<211> LENGTH: 111
```

```
<212> TYPE: PRT
<213> ORGANISM: Mus musculus

<400> SEQUENCE: 2

Met Ser Asp Ala Ala Val Asp Thr Ser Ser Glu Ile Thr Thr Lys Asp
1               5                   10                  15

Leu Lys Glu Lys Lys Glu Val Val Glu Ala Glu Asn Gly Arg Asp
                20                  25                  30

Ala Pro Ala Asn Gly Asn Ala Gln Asn Glu Glu Asn Gly Glu Gln Glu
            35                  40                  45

Ala Asp Asn Glu Val Asp Glu Glu Glu Glu Gly Gly Glu Glu Glu
            50                  55                  60

Glu Glu Glu Glu Glu Gly Asp Gly Glu Glu Asp Gly Asp Glu Asp
65                  70                  75                  80

Glu Glu Ala Glu Ala Pro Thr Gly Lys Arg Val Ala Glu Asp Asp
                85                  90                  95

Asp Asp Asp Val Asp Thr Lys Lys Gln Lys Thr Glu Glu Asp Asp
                100                 105                 110

<210> SEQ ID NO 3
<211> LENGTH: 112
<212> TYPE: PRT
<213> ORGANISM: Rattus norvegicus

<400> SEQUENCE: 3

Met Ser Asp Ala Ala Val Asp Thr Ser Ser Glu Ile Thr Thr Lys Asp
1               5                   10                  15

Leu Lys Glu Lys Lys Glu Val Val Glu Ala Glu Asn Gly Arg Asp
                20                  25                  30

Ala Pro Ala Asn Gly Asn Ala Gln Asn Glu Glu Asn Gly Glu Gln Glu
            35                  40                  45

Ala Asp Asn Glu Val Asp Glu Glu Glu Glu Gly Gly Glu Glu Glu
            50                  55                  60

Glu Glu Glu Glu Glu Gly Asp Gly Glu Glu Asp Gly Asp Glu Asp
65                  70                  75                  80

Glu Glu Ala Glu Ala Pro Thr Gly Lys Arg Val Ala Glu Asp Asp
                85                  90                  95

Asp Asp Asp Val Glu Thr Lys Lys Gln Lys Lys Thr Asp Glu Asp Asp
                100                 105                 110

<210> SEQ ID NO 4
<211> LENGTH: 30
<212> TYPE: PRT
<213> ORGANISM: Artificial Sequence
<220> FEATURE:
<223> OTHER INFORMATION: consensus amino acid sequence

<400> SEQUENCE: 4

Ala Asp Asn Glu Val Asp Glu Glu Glu Glu Gly Gly Glu Glu Glu
1               5                   10                  15

Glu Glu Glu Glu Glu Gly Asp Gly Glu Glu Asp Gly Asp
                20                  25                  30

<210> SEQ ID NO 5
<211> LENGTH: 25
<212> TYPE: PRT
<213> ORGANISM: Homo sapiens

<400> SEQUENCE: 5
```

```
Ala Asp Asn Glu Val Asp Glu Glu Glu Glu Gly Gly Glu Glu
 1               5                  10                  15

Gly Asp Gly Glu Glu Glu Asp Gly Asp
             20                  25
```

<210> SEQ ID NO 6
<211> LENGTH: 9
<212> TYPE: PRT
<213> ORGANISM: Artificial Sequence
<220> FEATURE:
<223> OTHER INFORMATION: consensus amino acid sequence

<400> SEQUENCE: 6

```
Glu Val Asp Glu Glu Glu Glu Glu Gly
 1               5
```

<210> SEQ ID NO 7
<211> LENGTH: 105
<212> TYPE: PRT
<213> ORGANISM: Homo sapiens

<400> SEQUENCE: 7

```
Met Ser Asp Ala Ala Val Asp Thr Ser Ser Glu Ile Thr Thr Glu Asp
 1               5                  10                  15

Leu Lys Glu Lys Lys Glu Val Val Glu Glu Ala Glu Asn Gly Arg Asp
                20                  25                  30

Ala Pro Ala His Gly Asn Ala Asn Glu Glu Asn Gly Glu Pro Glu Ala
            35                  40                  45

Asp Asn Glu Val Asp Glu Glu Glu Glu Gly Gly Glu Glu Glu Gly
         50                  55                  60

Asp Gly Glu Glu Glu Asp Gly Asp Glu Asp Gly Ala Glu Ser Ala
 65                  70                  75                  80

Thr Gly Lys Arg Ala Ala Glu Asp Asp Glu Asp Asp Val Asp Thr
                85                  90                  95

Gln Lys Gln Lys Thr Asp Glu Asp Asp
                100                 105
```

<210> SEQ ID NO 8
<211> LENGTH: 110
<212> TYPE: PRT
<213> ORGANISM: Homo sapiens

<400> SEQUENCE: 8

```
Met Ser Asp Ala Ala Val Asp Thr Ser Ser Glu Ile Thr Thr Lys Asp
 1               5                  10                  15

Leu Lys Glu Lys Lys Glu Val Val Glu Glu Ala Glu Asn Gly Arg Asp
                20                  25                  30

Ala Pro Ala Asn Gly Asn Ala Asn Glu Glu Asn Gly Glu Gln Glu Ala
            35                  40                  45

Asp Asn Glu Val Asp Glu Glu Glu Glu Gly Gly Glu Glu Glu Glu
         50                  55                  60

Glu Glu Glu Glu Gly Asp Gly Glu Glu Glu Asp Gly Asp Glu Asp Glu
 65                  70                  75                  80

Glu Ala Glu Ser Ala Thr Gly Lys Arg Ala Ala Glu Asp Asp Glu Asp
                85                  90                  95

Asp Asp Val Asp Thr Lys Lys Gln Lys Thr Asp Glu Asp Asp
                100                 105                 110
```

<210> SEQ ID NO 9

<211> LENGTH: 110
<212> TYPE: PRT
<213> ORGANISM: Homo sapiens

<400> SEQUENCE: 9

Met Ser Asp Ala Ala Val Asp Thr Ser Ser Glu Ile Thr Thr Lys Asp
1               5                   10                  15
Leu Lys Glu Lys Lys Glu Val Val Glu Glu Ala Glu Asn Gly Arg Asp
                20                  25                  30
Ala Pro Ala Asn Gly Asn Ala Asn Glu Glu Asn Gly Glu Gln Glu Ala
            35                  40                  45
Asp Asn Glu Val Asp Glu Glu Glu Glu Gly Gly Glu Glu Glu Glu
        50                  55                  60
Glu Glu Glu Glu Gly Asp Gly Glu Glu Val Asp Gly Asp Glu Asp Glu
65                  70                  75                  80
Glu Ala Glu Ser Ala Thr Gly Lys Arg Ala Ala Glu Asp Asp Glu Asp
                85                  90                  95
Asp Asp Val Asp Thr Lys Lys Gln Lys Thr Asp Glu Asp Asp
            100                 105                 110

<210> SEQ ID NO 10
<211> LENGTH: 110
<212> TYPE: PRT
<213> ORGANISM: Homo sapiens

<400> SEQUENCE: 10

Met Ser Asp Ala Ala Val Asp Thr Ser Ser Glu Ile Thr Thr Lys Asp
1               5                   10                  15
Leu Lys Glu Lys Lys Glu Val Val Glu Glu Ala Glu Asn Gly Arg Asp
                20                  25                  30
Ala Pro Ala Asn Gly Asn Ala Asn Glu Glu Asn Gly Glu Gln Glu Ala
            35                  40                  45
Asp Asn Glu Val Asp Glu Glu Glu Glu Gly Gly Glu Glu Glu Glu
        50                  55                  60
Glu Glu Glu Glu Gly Asp Gly Glu Glu Asp Gly Asp Glu Asp Glu
65                  70                  75                  80
Glu Ala Glu Ser Ala Thr Gly Lys Arg Ala Ala Glu Asp Asp Glu Asp
                85                  90                  95
Asp Asp Val Asp Thr Lys Lys Gln Lys Thr Asp Glu Asp Asp
            100                 105                 110

<210> SEQ ID NO 11
<211> LENGTH: 108
<212> TYPE: PRT
<213> ORGANISM: Homo sapiens

<400> SEQUENCE: 11

Met Ser Asp Ala Ala Val Asp Thr Ser Ser Glu Ile Thr Thr Glu Asp
1               5                   10                  15
Leu Lys Glu Lys Lys Glu Val Val Glu Ala Glu Asn Gly Arg Asp
                20                  25                  30
Ala Pro Ala Asn Arg Asn Ala Asn Glu Glu Asn Gly Glu Pro Glu Ala
            35                  40                  45
Asp Asn Glu Val Asp Glu Glu Glu Glu Gly Gly Glu Glu Glu Glu
        50                  55                  60
Glu Glu Glu Gly Asp Gly Glu Glu Asp Gly Asp Glu Asp Glu Gly
65                  70                  75                  80

```
Ala Glu Ser Ala Thr Gly Lys Arg Ala Glu Asp Asp Glu Asp Asp
                85                  90                  95

Asp Val Asp Thr Gln Lys Ser Glu Asp Arg Arg Gly
            100                 105
```

<210> SEQ ID NO 12
<211> LENGTH: 110
<212> TYPE: PRT
<213> ORGANISM: Homo sapiens

<400> SEQUENCE: 12

```
Met Ser Asp Ala Ala Val Asp Thr Ser Ser Glu Ile Thr Ile Lys Asp
1               5                   10                  15

Leu Lys Glu Lys Lys Glu Val Val Glu Glu Ala Glu Asn Gly Arg Asp
                20                  25                  30

Ala Pro Ala Asn Gly Asn Ala Asn Glu Glu Asn Gly Glu Gln Glu Ala
                35                  40                  45

Asp Ser Glu Val Asp Glu Glu Glu Glu Gly Gly Glu Glu Glu Glu
            50                  55                  60

Glu Glu Glu Glu Gly Asp Gly Glu Glu Asp Gly Asp Glu Asp Glu
65                  70                  75                  80

Glu Ala Glu Ser Pro Thr Gly Lys Arg Ala Glu Asp Asp Glu Asp
                85                  90                  95

Asp Asp Val Asp Thr Lys Lys Gln Lys Thr Glu Asp Asp
            100                 105                 110
```

<210> SEQ ID NO 13
<211> LENGTH: 109
<212> TYPE: PRT
<213> ORGANISM: Homo sapiens

<400> SEQUENCE: 13

```
Met Ser Asp Ala Ala Val Asp Thr Ser Ser Glu Ile Thr Thr Lys Asp
1               5                   10                  15

Leu Gln Glu Lys Lys Glu Val Val Glu Glu Ala Glu Asn Gly Arg Asp
                20                  25                  30

Ala Pro Ala Asn Gly Asn Ala Asn Glu Glu Asn Gly Glu Gln Glu Ala
                35                  40                  45

Asp Asn Glu Val Asp Glu Glu Glu Glu Gly Gly Glu Glu Glu Glu
            50                  55                  60

Glu Glu Glu Gly Asp Gly Glu Glu Asp Gly Asp Glu Asp Glu Glu
65                  70                  75                  80

Ala Glu Thr Ala Thr Gly Lys Arg Ala Ala Glu Asp Asp Glu Asp Asp
                85                  90                  95

Asp Val Asp Thr Lys Lys Gln Lys Thr Glu Asp Asp
            100                 105
```

<210> SEQ ID NO 14
<211> LENGTH: 73
<212> TYPE: PRT
<213> ORGANISM: Homo sapiens

<400> SEQUENCE: 14

```
Met Ser Asp Ala Ala Val Asp Thr Ser Ser Glu Ile Thr Thr Lys Asp
1               5                   10                  15

Leu Lys Glu Lys Lys Glu Val Val Glu Glu Ala Glu Asn Gly Arg Asp
                20                  25                  30

Ala Pro Ala Asp Glu Glu Asn Gly Glu Gln Glu Ala Asp Asn Glu Val
```

```
            35                  40                  45
Asp Glu Glu Gln Glu Glu Gly Glu Glu Glu Glu Glu Glu
    50                  55                  60

Gly Glu Gly Glu Glu Glu Gly Trp Arg
65                  70
```

<210> SEQ ID NO 15
<211> LENGTH: 110
<212> TYPE: PRT
<213> ORGANISM: Homo sapiens

<400> SEQUENCE: 15

```
Met Ser Asp Ala Ala Val Asp Thr Ser Ser Glu Ile Thr Thr Lys Asp
1               5                   10                  15

Leu Gln Glu Lys Lys Glu Val Val Glu Glu Ala Glu Asn Gly Arg Asp
                20                  25                  30

Ala Pro Ala Asn Gly Asn Ala Asn Glu Glu Asn Gly Glu Gln Glu Ala
            35                  40                  45

Asp Ser Glu Val Asp Glu Glu Glu Glu Gly Glu Glu Glu Glu
    50                  55                  60

Glu Glu Glu Glu Gly Asp Gly Glu Glu Asp Gly Asp Glu Asp
65                  70                  75                  80

Glu Ala Glu Ser Ala Thr Gly Lys Arg Ala Ala Glu Asp Asp Glu Asp
                85                  90                  95

Asp Asp Val Asp Thr Lys Lys Gln Lys Thr Asp Glu Asp Asp
            100                 105                 110
```

<210> SEQ ID NO 16
<211> LENGTH: 111
<212> TYPE: PRT
<213> ORGANISM: Homo sapiens

<400> SEQUENCE: 16

```
Met Ser Asp Ala Ala Val Asp Thr Ser Ser Glu Ile Thr Thr Lys Asp
1               5                   10                  15

Leu Lys Glu Lys Lys Glu Val Val Glu Glu Ala Glu Asn Gly Arg Asp
                20                  25                  30

Ala Pro Ala Asn Gly Asn Ala Glu Asn Glu Glu Asn Gly Glu Gln Glu
            35                  40                  45

Ala Asp Asn Glu Val Asp Glu Glu Glu Glu Gly Gly Glu Glu Glu
    50                  55                  60

Glu Glu Glu Glu Glu Gly Asp Gly Glu Glu Asp Gly Asp Glu Asp
65                  70                  75                  80

Glu Glu Ala Glu Ser Ala Thr Gly Lys Arg Ala Ala Glu Asp Asp Glu
                85                  90                  95

Asp Asp Asp Val Asp Thr Lys Lys Gln Lys Thr Asp Glu Asp Asp
            100                 105                 110
```

<210> SEQ ID NO 17
<211> LENGTH: 110
<212> TYPE: PRT
<213> ORGANISM: Homo sapiens

<400> SEQUENCE: 17

```
Met Ser Asp Ala Ala Val Asp Thr Ser Ser Glu Ile Thr Thr Lys Asp
1               5                   10                  15

Leu Lys Glu Lys Lys Glu Val Val Glu Glu Ala Glu Asn Gly Arg Asp
                20                  25                  30
```

```
Ala Pro Ala Asn Gly Asn Ala Asn Glu Glu Asn Gly Glu Gln Glu Ala
            35                  40                  45

Asp Asn Glu Val Asp Glu Glu Glu Glu Gly Gly Glu Glu Glu Glu Glu
        50                  55                  60

Glu Glu Glu Glu Gly Asp Gly Glu Glu Asp Gly Asp Glu Asp
65                  70                  75                  80

Glu Ala Glu Ser Ala Thr Gly Lys Arg Ala Ala Glu Asp Asp Glu Asp
                85                  90                  95

Asp Asp Val Asp Thr Lys Lys Gln Lys Thr Asp Glu Asp Asp
            100                 105                 110
```

<210> SEQ ID NO 18
<211> LENGTH: 111
<212> TYPE: PRT
<213> ORGANISM: Homo sapiens

<400> SEQUENCE: 18

```
Met Ser Asp Ala Ala Val Asp Thr Ser Ser Glu Ile Thr Thr Lys Asp
1               5                   10                  15

Leu Lys Glu Lys Lys Glu Val Val Glu Glu Ala Glu Asn Gly Arg Asp
            20                  25                  30

Ala Pro Ala Asn Gly Asn Ala Glu Asn Glu Glu Asn Gly Glu Gln Glu
            35                  40                  45

Ala Asp Asn Glu Val Asp Glu Glu Glu Glu Gly Gly Glu Glu Glu Glu
        50                  55                  60

Glu Glu Glu Glu Gly Asp Gly Glu Glu Asp Gly Asp Glu Asp
65                  70                  75                  80

Glu Glu Ala Glu Ser Ala Thr Gly Lys Arg Ala Ala Glu Asp Asp Glu
                85                  90                  95

Asp Asp Asp Val Asp Thr Lys Lys Gln Lys Thr Asp Glu Asp Asp
            100                 105                 110
```

<210> SEQ ID NO 19
<211> LENGTH: 110
<212> TYPE: PRT
<213> ORGANISM: Homo sapiens

<400> SEQUENCE: 19

```
Met Ser Asp Ala Ala Val Asp Thr Ser Ser Glu Ile Thr Thr Lys Asp
1               5                   10                  15

Leu Lys Glu Lys Lys Glu Val Val Glu Glu Ala Glu Asn Gly Arg Asp
            20                  25                  30

Ala Pro Ala Asn Gly Asn Ala Asn Glu Glu Asn Gly Glu Gln Glu Ala
            35                  40                  45

Asp Asn Glu Val Asp Glu Glu Glu Glu Gly Gly Glu Glu Glu Glu Glu
        50                  55                  60

Glu Glu Glu Glu Gly Asp Gly Glu Glu Asp Gly Asp Glu Asp
65                  70                  75                  80

Glu Ala Glu Ser Ala Thr Gly Lys Arg Ala Ala Glu Asp Asp Glu Asp
                85                  90                  95

Asp Asp Val Asp Thr Lys Lys Gln Lys Thr Asp Glu Asp Asp
            100                 105                 110
```

<210> SEQ ID NO 20
<211> LENGTH: 88
<212> TYPE: PRT
<213> ORGANISM: Homo sapiens

<400> SEQUENCE: 20

Met Ser Asp Ala Ala Val Asp Thr Ser Ser Glu Ile Thr Thr Lys Asp
1               5                   10                  15

Leu Lys Glu Lys Lys Glu Val Val Glu Glu Ala Glu Asn Gly Arg Asp
                20                  25                  30

Ala Pro Ala Asn Gly Asn Ala Asn Glu Glu Asn Gly Glu Gln Glu Ala
            35                  40                  45

Asp Asn Glu Val Asp Glu Glu Glu Glu Gly Gly Glu Glu Glu Glu
    50                  55                  60

Glu Glu Glu Glu Gly Asp Gly Glu Glu Asp Gly Asp Glu Asp
65                  70                  75                  80

Glu Ala Glu Ser Ala Thr Gly Lys
                85

<210> SEQ ID NO 21
<211> LENGTH: 110
<212> TYPE: PRT
<213> ORGANISM: Homo sapiens

<400> SEQUENCE: 21

Met Ser Asp Ala Ala Val Asp Thr Ser Ser Glu Ile Thr Thr Lys Asp
1               5                   10                  15

Leu Lys Glu Lys Lys Glu Val Val Glu Glu Ala Glu Asn Gly Arg Asp
                20                  25                  30

Ala Pro Ala Asn Gly Asn Ala Asn Glu Glu Asn Gly Glu Gln Glu Ala
            35                  40                  45

Asp Asn Glu Val Asp Glu Glu Glu Glu Gly Gly Glu Glu Glu Glu
    50                  55                  60

Glu Glu Glu Glu Gly Asp Gly Glu Glu Asp Gly Asp Glu Asp Glu
65                  70                  75                  80

Glu Ala Glu Ser Ala Thr Gly Lys Arg Ala Ala Glu Asp Asp Glu Asp
                85                  90                  95

Asp Asp Val Asp Thr Lys Lys Gln Lys Thr Asp Glu Asp Asp
            100                 105                 110

<210> SEQ ID NO 22
<211> LENGTH: 110
<212> TYPE: PRT
<213> ORGANISM: Homo sapiens

<400> SEQUENCE: 22

Met Ser Asp Ala Ala Val Asp Thr Ser Ser Glu Ile Thr Thr Lys Asp
1               5                   10                  15

Leu Lys Glu Lys Lys Glu Val Val Glu Glu Ala Glu Asn Gly Arg Asp
                20                  25                  30

Ala Pro Ala Asn Gly Asn Ala Asn Glu Glu Asn Gly Glu Gln Glu Ala
            35                  40                  45

Asp Asn Glu Val Asp Glu Glu Glu Glu Gly Gly Glu Glu Glu Glu
    50                  55                  60

Glu Glu Glu Glu Gly Asp Gly Glu Glu Asp Gly Asp Glu Asp Glu
65                  70                  75                  80

Glu Ala Glu Ser Ala Thr Gly Lys Arg Ala Ala Glu Asp Asp Glu Asp
                85                  90                  95

Asp Asp Val Asp Thr Lys Lys Gln Lys Thr Asp Glu Asp Asp
            100                 105                 110

<210> SEQ ID NO 23
<211> LENGTH: 110
<212> TYPE: PRT
<213> ORGANISM: Homo sapiens

<400> SEQUENCE: 23

Met Ser Asp Ala Ala Val Asp Thr Ser Ser Glu Ile Thr Thr Lys Asp
1               5                   10                  15

Leu Lys Glu Lys Lys Glu Val Val Glu Glu Ala Glu Asn Gly Arg Asp
            20                  25                  30

Ala Pro Ala Asn Gly Asn Ala Asn Glu Glu Asn Gly Glu Gln Glu Ala
        35                  40                  45

Asp Asn Glu Val Asp Glu Glu Glu Glu Gly Gly Glu Glu Glu Glu
    50                  55                  60

Glu Glu Glu Glu Gly Asp Gly Glu Glu Asp Gly Asp Glu Asp Glu
65                  70                  75                  80

Glu Ala Glu Ser Ala Thr Gly Lys Arg Ala Ala Glu Asp Asp Glu Asp
            85                  90                  95

Asp Asp Val Asp Thr Lys Lys Gln Lys Thr Asp Glu Asp Asp
            100                 105                 110

<210> SEQ ID NO 24
<211> LENGTH: 110
<212> TYPE: PRT
<213> ORGANISM: Homo sapiens

<400> SEQUENCE: 24

Met Ser Asp Ala Ala Val Asp Thr Ser Ser Glu Ile Thr Thr Lys Asp
1               5                   10                  15

Leu Lys Glu Lys Lys Glu Val Val Glu Glu Ala Glu Asn Gly Arg Asp
            20                  25                  30

Ala Pro Ala Asn Gly Asn Ala Asn Glu Glu Asn Gly Glu Gln Glu Ala
        35                  40                  45

Asp Asn Glu Val Asp Glu Glu Glu Glu Gly Gly Glu Glu Glu Glu
    50                  55                  60

Glu Glu Glu Glu Gly Asp Gly Glu Glu Asp Gly Asp Glu Asp Glu
65                  70                  75                  80

Glu Ala Glu Ser Ala Thr Gly Lys Arg Ala Ala Glu Asp Asp Glu Asp
            85                  90                  95

Asp Asp Val Asp Thr Lys Lys Gln Lys Thr Asp Glu Asp Asp
            100                 105                 110

<210> SEQ ID NO 25
<211> LENGTH: 111
<212> TYPE: PRT
<213> ORGANISM: Homo sapiens

<400> SEQUENCE: 25

Met Ser Asp Ala Ala Val Asp Thr Ser Ser Glu Ile Thr Thr Lys Asp
1               5                   10                  15

Leu Lys Glu Lys Lys Glu Val Val Glu Glu Ala Glu Asn Gly Arg Asp
            20                  25                  30

Ala Pro Ala Asn Gly Asn Ala Glu Asn Glu Glu Asn Gly Glu Gln Glu
        35                  40                  45

Ala Asp Asn Glu Val Asp Glu Glu Glu Glu Gly Gly Glu Glu Glu
    50                  55                  60

Glu Glu Glu Glu Glu Gly Asp Gly Glu Glu Glu Asp Gly Asp Glu Asp

```
                65                  70                  75                  80
Glu Glu Ala Glu Ser Ala Thr Gly Lys Arg Ala Ala Glu Asp Asp Glu
                85                  90                  95
Asp Asp Asp Val Asp Thr Lys Lys Gln Lys Thr Asp Glu Asp Asp
                100                 105                 110
```

```
<210> SEQ ID NO 26
<211> LENGTH: 110
<212> TYPE: PRT
<213> ORGANISM: Homo sapiens

<400> SEQUENCE: 26

Met Ser Asp Ala Ala Val Asp Thr Ser Ser Glu Ile Thr Thr Lys Asp
1               5                   10                  15
Leu Lys Glu Lys Lys Glu Val Val Glu Glu Ala Glu Asn Gly Arg Asp
                20                  25                  30
Ala Pro Ala Asn Gly Asn Ala Asn Glu Glu Asn Gly Glu Gln Glu Ala
                35                  40                  45
Asp Asn Glu Val Asp Glu Glu Glu Glu Gly Gly Glu Glu Glu Glu
            50                  55                  60
Glu Glu Glu Glu Gly Asp Gly Glu Glu Gly Gly Asp Glu Asp Glu
65                  70                  75                  80
Glu Ala Glu Ser Ala Thr Gly Lys Arg Ala Ala Glu Asp Asp Glu
                85                  90                  95
Asp Asp Val Asp Thr Lys Lys Gln Lys Thr Asp Glu Asp Asp
                100                 105                 110
```

```
<210> SEQ ID NO 27
<211> LENGTH: 110
<212> TYPE: PRT
<213> ORGANISM: Homo sapiens

<400> SEQUENCE: 27

Met Ser Asp Ala Ala Val Asp Thr Ser Ser Glu Ile Thr Thr Lys Asp
1               5                   10                  15
Leu Lys Glu Lys Lys Glu Val Val Glu Glu Ala Glu Asn Gly Arg Asp
                20                  25                  30
Ala Pro Ala Asn Gly Asn Ala Asn Glu Glu Asn Gly Glu Gln Glu Ala
                35                  40                  45
Asp Asn Glu Val Asp Glu Glu Glu Glu Gly Gly Glu Glu Glu Glu
            50                  55                  60
Glu Glu Glu Glu Gly Asp Gly Glu Glu Gly Gly Asp Glu Asp Glu
65                  70                  75                  80
Glu Ala Glu Ser Ala Thr Gly Lys Arg Ala Ala Glu Asp Asp Glu
                85                  90                  95
Asp Asp Val Asp Thr Lys Lys Gln Lys Thr Asp Glu Asp Asp
                100                 105                 110
```

```
<210> SEQ ID NO 28
<211> LENGTH: 101
<212> TYPE: PRT
<213> ORGANISM: Homo sapiens

<400> SEQUENCE: 28

Met Ser Asp Ala Ala Val Asp Thr Ser Ser Glu Ile Thr Thr Glu Asp
1               5                   10                  15
Leu Lys Glu Lys Lys Glu Val Val Glu Glu Ala Glu Asn Gly Arg Asp
                20                  25                  30
```

```
Ala Pro Ala Asp Glu Glu Asn Gly Glu Gln Glu Ala Asp Asn Glu Val
        35                  40                  45

Asp Glu Glu Gln Glu Glu Gly Glu Glu Glu Gly Asp Gly Glu Glu
    50                  55                  60

Glu Asp Gly Asp Glu Asp Glu Gly Ala Glu Ser Ala Thr Asp Lys Arg
65                  70                  75                  80

Ala Ala Glu Asp Asp Glu Asp Asn Asp Val Asp Thr Lys Lys Gln Lys
                85                  90                  95

Thr Asp Glu Asp Asp
            100

<210> SEQ ID NO 29
<211> LENGTH: 101
<212> TYPE: PRT
<213> ORGANISM: Homo sapiens

<400> SEQUENCE: 29

Met Ser Asp Ala Ala Val Asp Thr Ser Ser Glu Ile Thr Thr Glu Asp
1               5                   10                  15

Leu Lys Glu Lys Lys Glu Val Val Glu Glu Ala Glu Asn Gly Arg Asp
            20                  25                  30

Ala Pro Ala Asp Glu Glu Asn Gly Glu Gln Glu Ala Asp Asn Glu Val
        35                  40                  45

Asp Glu Glu Gln Glu Glu Gly Glu Glu Glu Gly Asp Gly Glu Glu
    50                  55                  60

Glu Asp Gly Asp Glu Asp Glu Gly Ala Glu Ser Ala Thr Asp Lys Arg
65                  70                  75                  80

Ala Ala Glu Asp Asp Glu Asp Asn Asp Val Asp Thr Lys Lys Gln Lys
                85                  90                  95

Thr Asp Glu Asp Asp
            100

<210> SEQ ID NO 30
<211> LENGTH: 112
<212> TYPE: PRT
<213> ORGANISM: Rattus norvegicus

<400> SEQUENCE: 30

Met Ser Asp Ala Ala Val Asp Thr Ser Ser Glu Ile Thr Thr Lys Asp
1               5                   10                  15

Leu Lys Glu Lys Lys Glu Val Val Glu Glu Ala Glu Asn Gly Arg Asp
            20                  25                  30

Ala Pro Ala Asn Gly Asn Ala Gln Asn Glu Glu Asn Gly Glu Gln Glu
        35                  40                  45

Ala Asp Asn Glu Val Asp Glu Glu Glu Glu Gly Gly Glu Glu Glu
    50                  55                  60

Glu Glu Glu Glu Glu Gly Asp Gly Glu Glu Asp Gly Asp Glu Asp
65                  70                  75                  80

Glu Glu Ala Glu Ala Pro Thr Gly Lys Arg Val Ala Glu Asp Glu
                85                  90                  95

Asp Asp Asp Val Glu Thr Lys Lys Gln Lys Thr Glu Asp Asp
            100                 105                 110

<210> SEQ ID NO 31
<211> LENGTH: 112
<212> TYPE: PRT
<213> ORGANISM: Rattus norvegicus
```

<400> SEQUENCE: 31

Met Ser Asp Ala Ala Val Asp Thr Ser Ser Glu Ile Thr Thr Lys Asp
1               5                   10                  15

Leu Lys Glu Lys Lys Glu Val Val Glu Glu Ala Glu Asn Gly Arg Asp
            20                  25                  30

Ala Pro Ala Asn Gly Asn Ala Gln Asn Glu Glu Asn Gly Glu Gln Glu
        35                  40                  45

Ala Asp Asn Glu Val Asp Glu Glu Glu Glu Gly Gly Glu Glu Glu Glu
    50                  55                  60

Glu Glu Glu Glu Glu Gly Asp Gly Glu Glu Asp Gly Asp Glu Asp
65                  70                  75                  80

Glu Glu Ala Glu Ala Pro Thr Gly Lys Arg Val Ala Glu Asp Asp Glu
            85                  90                  95

Asp Asp Asp Val Glu Thr Lys Lys Gln Lys Lys Thr Asp Glu Asp Asp
            100                 105                 110

<210> SEQ ID NO 32
<211> LENGTH: 112
<212> TYPE: PRT
<213> ORGANISM: Rattus norvegicus

<400> SEQUENCE: 32

Met Ser Asp Ala Ala Val Asp Thr Ser Ser Glu Ile Thr Thr Lys Asp
1               5                   10                  15

Leu Lys Glu Lys Lys Glu Val Val Glu Glu Ala Glu Asn Gly Arg Asp
            20                  25                  30

Ala Pro Ala Asn Gly Asn Ala Gln Asn Glu Glu Asn Gly Glu Gln Glu
        35                  40                  45

Ala Asp Asn Glu Val Asp Glu Glu Glu Glu Gly Gly Glu Glu Glu Glu
    50                  55                  60

Glu Glu Glu Glu Glu Gly Asp Gly Glu Glu Asp Gly Asp Glu Asp
65                  70                  75                  80

Glu Glu Ala Glu Ala Pro Thr Gly Lys Arg Val Ala Glu Asp Asp Glu
            85                  90                  95

Asp Asp Asp Val Glu Thr Lys Lys Gln Lys Lys Thr Asp Glu Asp Asp
            100                 105                 110

<210> SEQ ID NO 33
<211> LENGTH: 112
<212> TYPE: PRT
<213> ORGANISM: Rattus norvegicus

<400> SEQUENCE: 33

Met Ser Asp Ala Ala Val Asp Thr Ser Ser Glu Ile Thr Thr Lys Asp
1               5                   10                  15

Leu Lys Glu Lys Lys Glu Val Val Glu Glu Ala Glu Asn Gly Arg Asp
            20                  25                  30

Ala Pro Ala Asn Gly Asn Ala Gln Asn Glu Glu Asn Gly Glu Gln Glu
        35                  40                  45

Ala Asp Asn Glu Val Asp Glu Glu Glu Glu Gly Gly Glu Glu Glu Glu
    50                  55                  60

Glu Glu Glu Glu Glu Gly Asp Gly Glu Glu Asp Gly Asp Glu Asp
65                  70                  75                  80

Glu Glu Ala Glu Ala Pro Thr Gly Lys Arg Val Ala Glu Asp Asp Glu
            85                  90                  95

```
Asp Asp Asp Val Glu Thr Lys Lys Gln Lys Lys Thr Asp Glu Asp Asp
            100                 105                 110
```

<210> SEQ ID NO 34
<211> LENGTH: 112
<212> TYPE: PRT
<213> ORGANISM: Rattus norvegicus

<400> SEQUENCE: 34

```
Met Ser Asp Ala Ala Val Asp Thr Ser Ser Glu Ile Thr Thr Lys Asp
1               5                   10                  15

Leu Lys Glu Lys Lys Glu Val Val Glu Glu Ala Glu Asn Gly Arg Asp
            20                  25                  30

Ala Pro Ala Asn Gly Asn Ala Gln Asn Glu Glu Asn Gly Glu Gln Glu
        35                  40                  45

Ala Asp Asn Glu Val Asp Glu Glu Glu Glu Gly Gly Glu Glu Glu Glu
    50                  55                  60

Glu Glu Glu Glu Glu Gly Asp Gly Glu Glu Glu Asp Gly Asp Glu Asp
65                  70                  75                  80

Glu Glu Ala Glu Ala Pro Thr Gly Lys Arg Val Ala Glu Asp Asp Glu
                85                  90                  95

Asp Asp Asp Val Glu Thr Lys Lys Gln Lys Lys Thr Asp Glu Asp Asp
            100                 105                 110
```

<210> SEQ ID NO 35
<211> LENGTH: 87
<212> TYPE: PRT
<213> ORGANISM: Rattus norvegicus

<400> SEQUENCE: 35

```
Met Ser Asp Ala Ala Val Asp Thr Ser Ser Glu Ile Thr Thr Lys Asp
1               5                   10                  15

Leu Lys Glu Lys Lys Glu Val Val Glu Glu Ala Glu Asn Gly Arg Asp
            20                  25                  30

Ala Pro Ala Asn Gly Asn Ala Gln Asn Glu Glu Asn Gly Glu Gln Glu
        35                  40                  45

Ala Asp Asn Glu Val Asp Glu Glu Glu Glu Gly Gly Glu Glu Glu Glu
    50                  55                  60

Glu Glu Glu Glu Glu Gly Asp Gly Glu Glu Glu Asp Gly Asp Glu Asp
65                  70                  75                  80

Glu Glu Ala Gly Gln Lys Lys
                85
```

<210> SEQ ID NO 36
<211> LENGTH: 87
<212> TYPE: PRT
<213> ORGANISM: Rattus norvegicus

<400> SEQUENCE: 36

```
Met Ser Asp Ala Ala Val Asp Thr Ser Ser Glu Ile Thr Thr Lys Asp
1               5                   10                  15

Leu Lys Glu Lys Lys Glu Val Val Glu Glu Ala Glu Asn Gly Arg Asp
            20                  25                  30

Ala Pro Ala Asn Gly Asn Ala Gln Asn Glu Glu Asn Gly Glu Gln Glu
        35                  40                  45

Ala Asp Asn Glu Val Asp Glu Glu Glu Glu Gly Gly Glu Glu Lys
    50                  55                  60

Glu Glu Glu Lys Glu Gly Asp Gly Glu Glu Glu Asp Gly Asp Glu Asp
```

```
                    65                  70                  75                  80

Glu Glu Ala Gly Gln Lys Lys
                85

<210> SEQ ID NO 37
<211> LENGTH: 111
<212> TYPE: PRT
<213> ORGANISM: Mus musculus

<400> SEQUENCE: 37

Met Ser Asp Ala Ala Val Asp Thr Ser Ser Glu Ile Thr Thr Lys Asp
1               5                   10                  15

Leu Lys Glu Lys Lys Glu Val Val Glu Glu Ala Glu Asn Gly Arg Asp
            20                  25                  30

Ala Pro Ala Asn Gly Asn Ala Gln Asn Glu Glu Asn Gly Glu Gln Glu
        35                  40                  45

Ala Asp Asn Glu Val Asp Glu Glu Glu Glu Gly Gly Glu Glu Glu
    50                  55                  60

Glu Glu Glu Glu Glu Gly Asp Gly Glu Glu Asp Gly Asp Glu Asp
65                  70                  75                  80

Glu Glu Ala Glu Ala Pro Thr Gly Lys Arg Val Ala Glu Asp Asp
            85                  90                  95

Asp Asp Asp Val Asp Thr Lys Lys Gln Lys Thr Glu Glu Asp
        100                 105                 110

<210> SEQ ID NO 38
<211> LENGTH: 101
<212> TYPE: PRT
<213> ORGANISM: Mus musculus

<400> SEQUENCE: 38

Met Ser Asp Glu Ala Val Asp Thr Ser Ser Glu Ile Thr Thr Lys Asp
1               5                   10                  15

Leu Asn Glu Lys Glu Val Val Glu Glu Ala Glu Ser Gly Arg Asp
            20                  25                  30

Ala Pro Ala Asn Gly Asn Ala Gln Asn Glu Glu Asn Gly Glu Gln Glu
        35                  40                  45

Ala Gly Asn Glu Val Asp Glu Glu Glu Glu Gly Asp Gly Glu Glu
    50                  55                  60

Glu Asp Gly Asp Glu Asp Glu Ala Glu Ala Pro Thr Gly Lys Arg
65                  70                  75                  80

Val Ala Glu Asp Asp Glu Asp Asp Val Asp Thr Lys Lys Gln Lys
            85                  90                  95

Thr Glu Glu Asp Asp
        100

<210> SEQ ID NO 39
<211> LENGTH: 73
<212> TYPE: PRT
<213> ORGANISM: Mus musculus

<400> SEQUENCE: 39

Met Ser Asp Ala Ala Val Asp Thr Ser Ser Glu Ile Thr Thr Lys Asp
1               5                   10                  15

Leu Lys Glu Lys Lys Glu Val Val Glu Glu Ala Glu Asn Gly Arg Asp
            20                  25                  30

Ala Pro Ala Asn Gly Asn Ala Gln Glu Asp Glu Glu Ala Glu Ala Pro
        35                  40                  45
```

```
Thr Gly Lys Arg Val Ala Glu Asp Glu Asp Asp Val Asp Thr
        50                  55                  60
Lys Lys Gln Lys Thr Glu Asp Asp
 65                  70

<210> SEQ ID NO 40
<211> LENGTH: 111
<212> TYPE: PRT
<213> ORGANISM: Mus musculus

<400> SEQUENCE: 40

Met Ser Asp Ala Ala Val Asp Thr Ser Ser Glu Ile Thr Thr Lys Asp
 1               5                  10                  15

Leu Lys Glu Lys Lys Glu Val Val Glu Glu Ala Glu Asn Gly Arg Asp
                20                  25                  30

Ala Pro Ala Asn Gly Asn Ala Gln Asn Glu Glu Asn Gly Glu Gln Glu
            35                  40                  45

Ala Asp Asn Glu Val Asp Glu Glu Glu Glu Gly Gly Glu Glu Glu
        50                  55                  60

Glu Glu Glu Glu Glu Gly Asp Gly Glu Glu Asp Gly Asp Glu Asp
 65                  70                  75                  80

Glu Glu Ala Glu Ala Pro Thr Gly Lys Arg Val Ala Glu Asp Asp Glu
                85                  90                  95

Asp Asp Asp Val Asp Thr Lys Lys Gln Lys Thr Glu Glu Asp Asp
                100                 105                 110

<210> SEQ ID NO 41
<211> LENGTH: 111
<212> TYPE: PRT
<213> ORGANISM: Mus musculus

<400> SEQUENCE: 41

Met Ser Asp Ala Ala Val Asp Thr Ser Ser Glu Ile Thr Thr Lys Asp
 1               5                  10                  15

Leu Lys Glu Lys Lys Glu Val Val Glu Glu Ala Glu Asn Gly Arg Asp
                20                  25                  30

Ala Pro Ala Asn Gly Asn Ala Gln Asn Glu Glu Asn Gly Glu Gln Glu
            35                  40                  45

Ala Asp Asn Glu Val Asp Glu Glu Glu Glu Gly Gly Glu Glu Glu
        50                  55                  60

Glu Glu Glu Glu Glu Gly Asp Gly Glu Glu Asp Gly Asp Glu Asp
 65                  70                  75                  80

Glu Glu Ala Glu Ala Pro Thr Gly Lys Arg Val Ala Glu Asp Asp Glu
                85                  90                  95

Asp Asp Asp Val Asp Thr Lys Lys Gln Lys Thr Glu Glu Asp Asp
                100                 105                 110

<210> SEQ ID NO 42
<211> LENGTH: 105
<212> TYPE: PRT
<213> ORGANISM: Danio rerio

<400> SEQUENCE: 42

Met Ala Asp Thr Lys Val Asp Thr Asn Lys Asp Val Ser Ala Lys Asp
 1               5                  10                  15

Leu Lys Glu Lys Lys Gln Val Glu Glu Ala Glu Asn Gly Lys Asp Ala
                20                  25                  30
```

```
Pro Ala Asn Gly Asn Ala Glu Asn Glu Glu Asn Gly Asp Gln Glu Asn
         35                  40                  45

Glu Val Asp Glu Glu Asp Asp Val Ala Glu Glu Asp Glu Glu Asp
 50                  55                  60

Asp Gly Glu Gly Asp Asp Asp Glu Asp Glu Ala Glu Gly Gly
 65                  70                  75                  80

Thr Gly Lys Arg Ala Ala Glu Asp Asp Asp Asp Glu Asp Asp Val
                 85                  90                  95

Asp Pro Lys Lys Gln Lys Thr Asp Val
            100                 105
```

<210> SEQ ID NO 43
<211> LENGTH: 109
<212> TYPE: PRT
<213> ORGANISM: Rana catesbeiana

<400> SEQUENCE: 43

```
Met Ser Asp Thr Ser Val Asp Ala Ser Val Glu Lys Thr Thr Lys Asp
 1               5                  10                  15

Leu Lys Ser Lys Asp Lys Glu Leu Val Glu Glu Thr Glu Asn Gly Lys
            20                  25                  30

Asp Lys Pro Ala Asn Gly Asn Ala Glu Asn Glu Glu Asn Gly Glu Asp
         35                  40                  45

Gly Ala Asp Asn Glu Glu Glu Glu Val Asp Glu Glu Asp Glu Glu
 50                  55                  60

Asp Glu Gly Glu Gly Asp Asp Asp Glu Gly Asp Glu Asp Glu Ala
 65                  70                  75                  80

Asp Gly Ala Thr Gly Lys Arg Ala Ala Glu Asp Asp Asp Glu Asp Asp
                 85                  90                  95

Asp Val Asp Ala Lys Lys Gln Lys Thr Asp Asp Asp Asp
            100                 105
```

<210> SEQ ID NO 44
<211> LENGTH: 28
<212> TYPE: PRT
<213> ORGANISM: Artificial Sequence
<220> FEATURE:
<223> OTHER INFORMATION: consensus amino acid sequence

<400> SEQUENCE: 44

```
Ser Asp Ala Ala Val Asp Thr Ser Ser Glu Ile Thr Thr Lys Asp Leu
 1               5                  10                  15

Lys Glu Lys Lys Glu Val Val Glu Glu Ala Glu Asn
            20                  25
```

<210> SEQ ID NO 45
<211> LENGTH: 30
<212> TYPE: PRT
<213> ORGANISM: Artificial Sequence
<220> FEATURE:
<223> OTHER INFORMATION: artificial peptide

<400> SEQUENCE: 45

```
Ala Ala Asn Glu Val Asp Glu Glu Glu Glu Gly Gly Glu Glu Glu
 1               5                  10                  15

Glu Glu Glu Glu Glu Gly Asp Gly Glu Glu Asp Gly Asp
            20                  25                  30
```

<210> SEQ ID NO 46
<211> LENGTH: 30

```
<212> TYPE: PRT
<213> ORGANISM: Artificial Sequence
<220> FEATURE:
<223> OTHER INFORMATION: artificial peptide

<400> SEQUENCE: 46

Ala Asp Ala Glu Val Asp Glu Glu Glu Glu Gly Gly Glu Glu Glu
1               5                   10                  15
Glu Glu Glu Glu Glu Gly Asp Gly Glu Glu Asp Gly Asp
                20                  25                  30

<210> SEQ ID NO 47
<211> LENGTH: 30
<212> TYPE: PRT
<213> ORGANISM: Artificial Sequence
<220> FEATURE:
<223> OTHER INFORMATION: artificial peptide

<400> SEQUENCE: 47

Ala Asp Asn Ala Val Asp Glu Glu Glu Glu Gly Gly Glu Glu Glu
1               5                   10                  15
Glu Glu Glu Glu Glu Gly Asp Gly Glu Glu Asp Gly Asp
                20                  25                  30

<210> SEQ ID NO 48
<211> LENGTH: 20
<212> TYPE: PRT
<213> ORGANISM: Artificial Sequence
<220> FEATURE:
<223> OTHER INFORMATION: artificial peptide

<400> SEQUENCE: 48

Glu Gly Gly Glu Glu Glu Glu Glu Glu Glu Gly Asp Gly Glu Glu
1               5                   10                  15
Glu Asp Gly Asp
                20

<210> SEQ ID NO 49
<211> LENGTH: 20
<212> TYPE: PRT
<213> ORGANISM: Artificial Sequence
<220> FEATURE:
<223> OTHER INFORMATION: artificial peptide

<400> SEQUENCE: 49

Asp Glu Glu Glu Glu Glu Gly Gly Glu Glu Glu Glu Glu Glu Glu
1               5                   10                  15
Gly Asp Gly Glu
                20

<210> SEQ ID NO 50
<211> LENGTH: 11
<212> TYPE: PRT
<213> ORGANISM: Artificial Sequence
<220> FEATURE:
<223> OTHER INFORMATION: artificial peptide

<400> SEQUENCE: 50

Thr Lys Lys Gln Lys Lys Thr Asp Glu Asp Asp
1               5                   10
```